United States Patent
Fulkerson et al.

(10) Patent No.: US 9,968,725 B2
(45) Date of Patent: May 15, 2018

(54) PRIMING SYSTEM AND METHOD OF DIALYSIS SYSTEMS

(71) Applicant: Fresenius Medical Care Holdings, Inc., Waltham, MA (US)

(72) Inventors: Barry Neil Fulkerson, Longmont, CO (US); Martin Hering, Irvine, CA (US); Frank Isackson, Monrovia, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 136 days.

(21) Appl. No.: 15/044,194

(22) Filed: Feb. 16, 2016

(65) Prior Publication Data

US 2017/0021085 A1    Jan. 26, 2017

Related U.S. Application Data

(63) Continuation of application No. 13/372,202, filed on Feb. 13, 2012, now Pat. No. 9,295,772, which is a continuation of application No. 12/575,450, filed on Oct. 7, 2009, now Pat. No. 8,137,553, which is a continuation-in-part of application No. 12/324,924, filed on Nov. 28, 2008, now Pat. No. 8,114,288.

(60) Provisional application No. 61/103,274, filed on Oct. 7, 2008, provisional application No. 61/021,962, filed
(Continued)

(51) Int. Cl.
| | |
|---|---|
| *A61M 1/36* | (2006.01) |
| *A61M 1/34* | (2006.01) |
| *A61M 1/16* | (2006.01) |

(52) U.S. Cl.
CPC ........ *A61M 1/3643* (2013.01); *A61M 1/1696* (2013.01); *A61M 1/342* (2013.01); *A61M 1/3437* (2014.02); *A61M 1/3465* (2014.02); *A61M 1/3647* (2014.02); *A61M 1/3649* (2014.02); *A61M 1/3672* (2013.01); *A61M 1/16* (2013.01); *A61M 2205/128* (2013.01); *A61M 2205/3324* (2013.01); *A61M 2205/3331* (2013.01); *A61M 2205/3368* (2013.01); *A61M 2205/3372* (2013.01); *Y10T 137/0491* (2015.04)

(58) Field of Classification Search
None
See application file for complete search history.

(56) References Cited

U.S. PATENT DOCUMENTS

| | | | | |
|---|---|---|---|---|
| 4,661,246 | A | * | 4/1987 | Ash .................................. 210/87 |
| 5,259,961 | A | * | 11/1993 | Eigendorf ..................... 210/646 |
| 5,591,344 | A | * | 1/1997 | Kenley et al. ................ 210/636 |

(Continued)

FOREIGN PATENT DOCUMENTS

WO    2008053259 A1    5/2008

OTHER PUBLICATIONS

Extended European Search Report for Application No. EP09819849.2, dated Jul. 21, 2017.

*Primary Examiner* — Krishnan S Menon
(74) *Attorney, Agent, or Firm* — Novel IP

(57) ABSTRACT

The application is directed to an extracorporeal blood processing system capable of using dialysate to prime the system. A plastic molded compact manifold supports molded blood and dialysate fluidic pathways along with relevant sensors, valves and pumps. The compact manifold is also disposable in one embodiment and can be detachably installed in the dialysis machine. A two-way valve in the manifold is used to direct the dialysate flow through the blood circuit to prime the circuit for use in treatment.

20 Claims, 16 Drawing Sheets

Related U.S. Application Data on Jan. 18, 2008, provisional application No. 60/990,959, filed on Nov. 29, 2007.

(56) References Cited

U.S. PATENT DOCUMENTS

| | | | |
|---|---|---|---|
| 2009/0107902 A1* | 4/2009 | Childers et al. | 210/196 |
| 2010/0133153 A1* | 6/2010 | Beden et al. | 210/85 |

\* cited by examiner

PRIMING SYSTEM AND METHOD OF DIALYSIS SYSTEMS

CROSS-REFERENCE TO RELATED APPLICATIONS

The present application is a continuation of U.S. patent application Ser. No. 12/575,450, filed on Oct. 7, 2009, which is a continuation in part of co-pending U.S. patent application Ser. No. 12/324,924, which relies on, for priority, U.S. Provisional Patent Application No. 60/990,959, entitled "System and Method of Changing Fluidic Circuit Between Hemodialysis Protocol and Hemofiltration Protocol", filed on Nov. 29, 2007 and U.S. Provisional Patent Application No. 61/021,962, of the same title, filed on Jan. 18, 2008. U.S. patent application Ser. No. 12/324,924 is incorporated herein by reference. Still further, the present invention incorporates by reference co-pending U.S. patent application Ser. No. 12/237,914, entitled "Manifolds for Use In Conducting Dialysis" and filed on Sep. 25, 2008 and U.S. patent application Ser. No. 12/245,397, entitled "Wearable Dialysis Systems and Methods", filed on Oct. 3, 2008. Still further, the present application relies on U.S. Provisional Application No. 61/103,274, filed on Oct. 7, 2008, for priority and is herein incorporated by reference.

FIELD

The present specification is directed to systems and methods for priming a blood circuit with dialysate and, in particular, to a disposable manifold that can be automatically switched between a priming mode of operation and a treatment mode of operation.

BACKGROUND

Hemodialysis is used for removing toxic wastes from the human body in cases of renal failure. The patient's blood is temporarily brought outside of the body via tubes and passed through at least one semi-permeable membrane, which may be a group of hollow fibers, in a dialyzer. The semi-permeable membrane separates the blood from a dialysate solution. Impurities from the blood pass through the membrane and into the dialysate solutions, primarily by osmotic pressure. The cleansed blood is then returned to the body.

Standard dialysis treatment, using an installed apparatus in hospitals, comprises two phases, namely, (a) dialysis, in which toxic substances and scoriae (normally small molecules) pass through the semi-permeable membrane from the blood to the dialysis liquid, and (b) ultrafiltration, in which a pressure difference between the blood circuit and the dialysate circuit, more precisely a reduced pressure in the latter circuit, causes the blood content of water to be reduced by a predetermined amount.

Dialysis procedures using standard equipment tend to be cumbersome as well as costly, besides requiring the patient to be bound to a dialysis center for long durations. Conventional systems are also less reliable because of the necessity of using a myriad of tubes comprising the fluid circuits of the purification systems, thus increasing the risks of leakage and breakage. Accordingly there is need in the art for an extra-corporeal blood processing system that can be operated in hemodialysis as well as hemofiltration modes, while at the same time offering reasonable portability to the patient. Such a portable dialysis system should also be conducive to using disposable components. Further, there is also a need for novel manifolds for dialysis systems with integrated blood purification system components, such as sensors, pumps and disposables, as well as molded blood and dialysate flow paths to avoid a complicated mesh of tubing and to enhance the robustness of the system.

Conventional sorbent-based dialysis systems require the blood side of the disposable dialysis circuit to be primed with sterile saline before each treatment prior to allowing the patient's blood to enter the circuit. This is an important first step to purge the system of any air. In operation, the patient's blood enters tubing filled with the saline solution and "chases" the saline solution to waste, after which dialysis begins. U.S. Pat. No. 4,661,246 describes a typical single access dialysis instrument having a single catheter for receiving body liquids, a dialyzer having a body liquid side with fluid inlet and fluid outlet connected to the catheter and further having a dialysate side with a dialysate inlet and a dialysate outlet. The dialysis instrument described also includes storage means for holding a supply of liquid, including dialysate for use in the dialyzer.

US Patent application No. 20020017489 and U.S. Pat. No. 6,187,198 describe systems and methods of priming a blood processing circuit in which both the retention of undesirable air bubbles and the risk of contamination is reduced.

US Patent application No. 20020017489 provides an arterial set and a venous set for blood flow between a blood processing unit and a patient. Each set has a main tube which carries a chamber in in-line flow relationship, and a branch tube extending from the chamber to empty into a drain receptacle. A portion of the branch tube extends through an upper wall of the chamber and projects for a distance into the chamber to spontaneously create an air bubble of desired operating volume above a liquid level in the chamber. The patent application describes a method of priming by passing a priming solution in a first direction of flow through at least one of the sets, to cause the priming solution to enter an in-line chamber carried by the one set in a flow direction that is retrograde to the normal direction of blood flow through the chamber. Next, the steps of removing air from the one set through a port and passing the priming solution in a reverse direction of flow to the first direction are performed preferably simultaneously in order to complete priming of the blood processing unit.

US Patent Application 20070185430 provides a system and method for producing purified replacement fluid in a unit used for renal replacement therapy on a patient. The system can be used both to purify non-purified fluid and to further purify sterile fluid contaminated (e.g., by touch contamination) during connection. The method employs the use of a filter with a membrane, having a pore size smaller than the non-purified and pyrogenic material to be filtered, separating a waste side of the filter from a clean side, and a pump in fluid communication with a container of a replacement fluid in fluid communication with the waste side of the filter, and a second container for holding purified replacement fluid in fluid communication with the clean side of the filter. The pump switches between a first direction that pumps fluid out of the first container and a second direction that removes waste from blood.

All of the above mentioned patents and patent applications describe various dialysis circuits and priming methods and are incorporated herein by reference.

Conventionally, the priming procedure requires a minimum of a liter of priming fluid such as saline, a clamp, tubing, connectors and a pole from which to hang the bag. A patient, or healthcare provider, must connect the line, open the clamp, close the clamp and dispose of the waste. This is a problem because a) it requires a high skill level to set up and manage the priming procedure and b) it requires extra materials. It would be preferred to use a more convenient priming fluid source and to simplify the priming procedure such that trained health care professionals are not required to manage and/or handle the priming process.

SUMMARY OF THE INVENTION

The Present Specification Discloses

The present specification further discloses a dialysis treatment system capable of operating in a priming mode and a treatment mode, comprising a housing defining a cavity, which is capable of receiving a manifold. The manifold comprises a plastic substrate comprising a first layer and a second layer; a first flow path defined by a first surface of the first layer and a first surface of the second layer; a second flow path defined by a first surface of the first layer and a first surface of the second layer; a valve in fluid communication with both said first flow path and said second flow path wherein said valve has first state and a second state and wherein, when in said first state, the first flow path and second flow path are in fluid isolation and when in said second state, the first flow path and second flow path are in fluid communication; and a valve interface physically attached to said housing, wherein said valve interface is configured to transmit a signal to said valve to cause said valve to switch between said first state and said second state.

Optionally, the manifold further comprises a first pump outlet, wherein said first pump outlet receives blood being pumped by a first pump, and a second pump outlet, wherein said second pump outlet receives dialysate being pumped by a second pump. Optionally, the valve is located adjacent said first pump outlet and said second pump outlet. Optionally, the valve is in said first state, the first pump outlet and second pump outlet are in fluid isolation from each other. Optionally, when the valve is in said second state, the first pump outlet and second pump outlet are in fluid communication with each other. Optionally, the dialysis treatment system further comprises a controller, wherein said controller generates the signal to cause said valve to switch between said first state and said second state. In one embodiment, the controller generates a signal to cause said valve to switch from said first state to said second state in response to a command for the dialysis treatment system to operate in priming mode. In another embodiment, the controller generates a signal to cause said valve to switch from said second state to said first state in response to a command for the dialysis treatment system to operate in treatment mode. The dialysis treatment system further comprises a dialysate reservoir and the priming of said manifold is effectuated using dialysate from said dialysate reservoir and not from a separate source of priming fluid.

In another embodiment, the present specification discloses a manifold capable of operating in a priming mode and a treatment mode, comprising a plastic substrate comprising a first layer and a second layer; a first flow circuit defined by a first surface of the first layer and a first surface of the second layer; a second flow circuit defined by a first surface of the first layer and a first surface of the second layer; a valve in fluid communication with both said first flow circuit and said second flow circuit wherein said valve has first state and a second state and wherein, when in said first state, fluid from said first flow circuit and cannot enter into said second flow circuit and when in said second state, fluid from said first flow circuit can enter into second flow circuit; and an interface to receive a signal from a signal source to cause said valve to switch between said first state and said second state.

Optionally, the interface causes said valve to switch from said first state to said second state in response to a signal to operate in priming mode. Optionally, the interface causes said valve to switch from said first state to said second state in response to a signal to operate in treatment mode.

In another embodiment, the present specification discloses a priming process for priming a manifold within a dialysis machine for use in a dialysis treatment, comprising the steps of: a) inserting said manifold into the dialysis machine, wherein said manifold comprises a blood circuit and a dialysate circuit, each defined by a substrate, and a valve in fluid communication with each of said blood circuit and dialysate circuit, wherein said valve has first state and a second state and wherein, when in said first state, fluid from the dialysate circuit cannot enter into the blood circuit and when in said second state, fluid from the dialysate circuit can enter into the blood circuit; b) placing said valve in said second state; c) pumping dialysate through said blood circuit; d) placing said valve in said first state; and e) removing dialysate from said blood circuit.

Optionally, the dialysate is pumped from a dialysate reservoir and not from a separate source of priming fluid. Optionally, the valve is placed in said first state or second state by communicating a signal from a controller located within the dialysis machine.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

Figure 1:
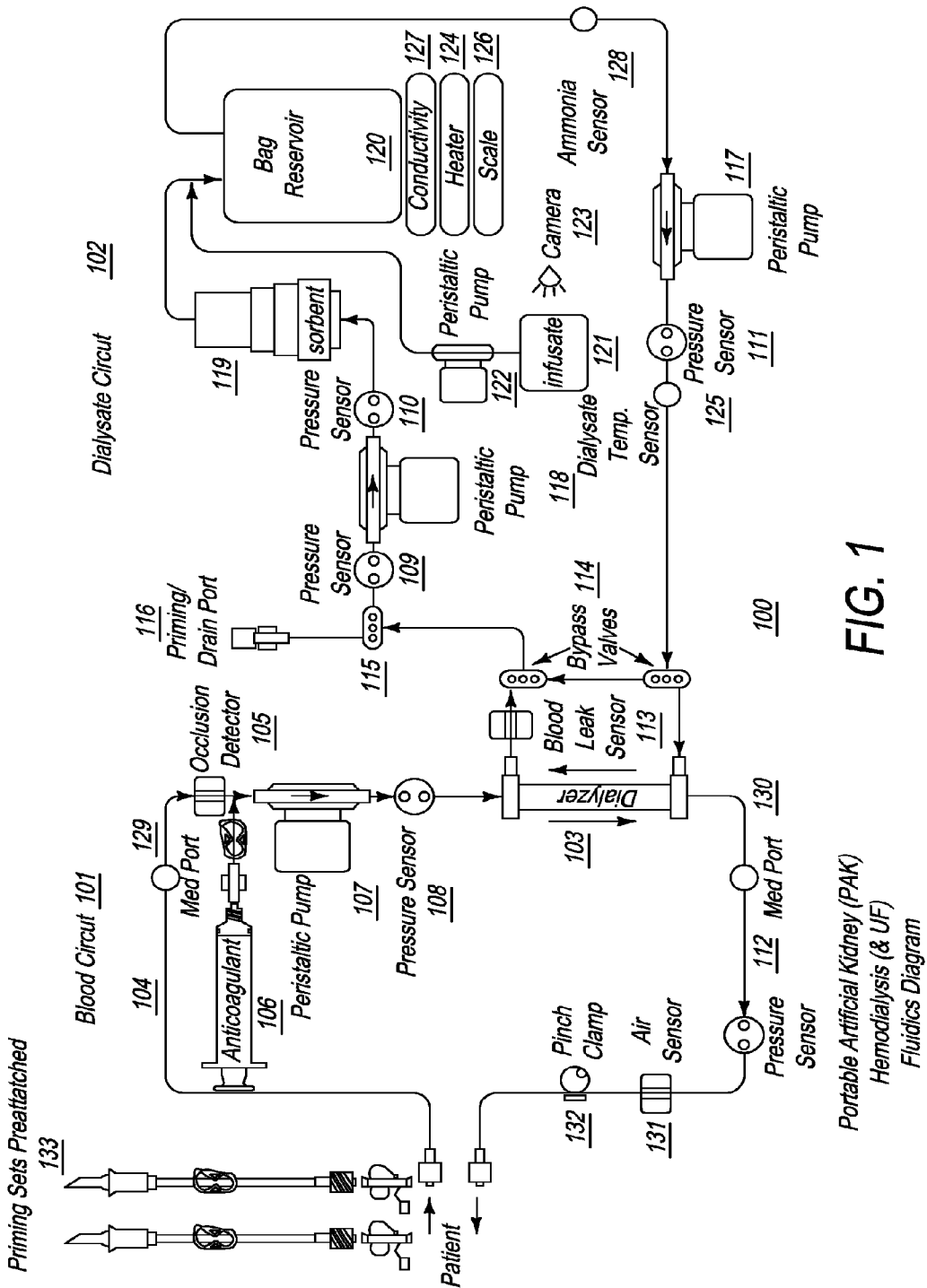
FIG. 1 shows an exemplary fluidic circuit for an extracorporeal blood processing system.

While the present specification discloses embodiments in many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribe treatment plan.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The present invention eliminates the need to have a separate bag of sterile saline and its associated hardware. In one embodiment, the present invention employs sorbent-generated dialysate, created when the dialysate side of the circuit is primed, as the priming fluid for the blood side. For purposes of explaining the invention, an exemplary manifold in which the priming methods and systems of the present invention shall first be described.

FIG. 1 shows the fluidic circuit for an extracorporeal blood processing system 100, used for conducting hemodialysis and hemofiltration. In one embodiment of the present invention, the system 100 is implemented as a portable artificial kidney (PAK), which may be used by a patient for conducting dialysis at home.

Referring to FIG. 1, the hemodialysis system comprises two circuits—a Blood Circuit 101 and a Dialysate Circuit 102. Blood treatment during dialysis involves extracorporeal circulation through an exchanger having a semi permeable membrane—the hemodialyser or dialyzer 103. The patient's blood is circulated in the blood circuit 101 on one side of the membrane (dialyzer) 103 and a dialysis liquid called the dialysate, comprising the main electrolytes of the blood in concentrations prescribed by a physician, is circulated on the other side in the dialysate circuit 102. The circulation of dialysate fluid thus provides for the regulation and adjustment of the electrolytic concentration in blood.

The line 104 from the patient which feeds impure blood to the dialyzer 103 in the blood circuit 101 is provided with an occlusion detector 105 which is generally linked to a visual or audible alarm (not shown) to signal any obstruction to the blood flow. In order to prevent coagulation of blood, means 106, such as a pump, syringe, or any other injection device, for injecting an anticoagulant—such as heparin, into the blood are also provided. A peristaltic pump 107 is also provided to ensure flow of blood in the normal (desired) direction.

A pressure sensor 108 is provided at the inlet where impure blood enters the dialyzer 103. Other pressure sensors 109, 110, 111 and 112 are provided at various positions in the haemodialysis system that help keep track of and maintain fluid pressure at vantage points.

At the point where used dialysate fluid from the dialyzer 103 enters the dialysate circuit 102, a blood leak sensor 113 is provided to sense and warn of any leakage of blood cells into the dialysate circuit. A pair of bypass valves 114 is also provided at the beginning and end points of the dialysate circuit, so that under conditions of start up, or other as deemed necessary by the operator, the dialyzer can be bypassed from the dialysate fluid flow but that flow maintained. Another valve 115 is provided just before a priming/drain port 116. The port 116 is used for initially filling the circuit with a dialysate solution, and to remove used dialysate fluid after and in some instances during dialysis. Durring dialysis, valve 115 may be used to replace portions of used dialysate with high concentrations of for instance sodium with replenishment fluid of appropriate concentration so that overall component concentration of the dialysate is maintained at a desired level.

The dialysate circuit is provided with two peristaltic pumps 117 and 118. Pump 117 is used for pumping dialysate fluid to the drain or waste container, as well as for pumping regenerated dialysate into the dialyzer 103. Pump 118 is used for pumping out spent dialysate from the dialyzer 103, and pressuring it through the sorbent 119 and also for pumping in the dialysis fluid from port 116 for filling the system or maintaining component concentration in the dialysate.

A sorbent type cartridge 119 is provided in the dialysate circuit, which contains several layers of materials, each having a specific role in removing impurities such as urea and creatinine. The combination of these materials allows water suitable for drinking to be charged into the system for use as dialysate fluid. It also allows closed loop dialysis. That is, the sorbent cartridge enables regeneration of fresh dialysate from the spent dialysate coming from the dialyzer. For the fresh dialysate fluid, a lined container or reservoir 120 of a suitable capacity such as 0.5, 1, 5, 8 or 10 liters is provided. Depending upon patient requirement based on physician prescription, desired quantities of an infusate solution 121 can be added to the dialysis fluid. Infusate 121 is a solution containing minerals and/or glucose that help replenish minerals like potassium and calcium in the dialysate fluid at levels after undesired removal by the sorbent. A peristaltic pump 122 is provided to pump the desired amount of infusate solution to the container 120. A camera 123 may optionally be provided to monitor the changing liquid level of the infusate solution as a safety check warning of infusate flow failure.

A heater 124 is provided to maintain the temperature of dialysate fluid in the container 120 at the required level. The temperature of the dialysate fluid can be sensed by the temperature sensor 125 located just prior to the fluids entry in to the dialyzer. The container 120 is also equipped with a scale 126 for keeping track of the weight, and therefore volume, of the fluid in the container, and a conductivity sensor 127, which displays the conductivity of the dialysate fluid. The conductivity sensor 127 provides an indication of the level of sodium in the dialysate.

A medical port 129 is provided before blood from the patient enters the system for dialysis. Another medical port 130 is provided before clean blood from the dialyzer is returned to the patient. An air (or bubble) sensor 131 and a pinch clamp 132 are employed in the circuit to detect and prevent any air, gas or gas bubbles from being returned to the patient.

Priming set(s) 133 is/are attached to the hemodialysis system that help prepare the system by filling the blood circuit with sterile saline before it is used for dialysis. Priming set(s) may consist of short segments of tubing with IV bag spikes or IV needles or a combination of both pre-attached.

One of ordinary skill in the art would infer from the above discussion that the fluidic circuit for a hemodialysis that a hemodialoysis and/or hemofiltration system is a complex one and incorporates several elements. If implemented in a conventional manner, the system would manifest as a mesh of tubing and would be too complicated for a home dialysis user to configure and use.

Therefore, in order to make the system simple and easy to use at home by a patient, the present invention implements the system as a compact manifold in which most components of the fluidic circuit shown in FIG. 1 are integrated in a single piece of molded plastic or multiple pieces of molded plastic which are configured to connect together to form a single operative manifold structure.

Figure 2:
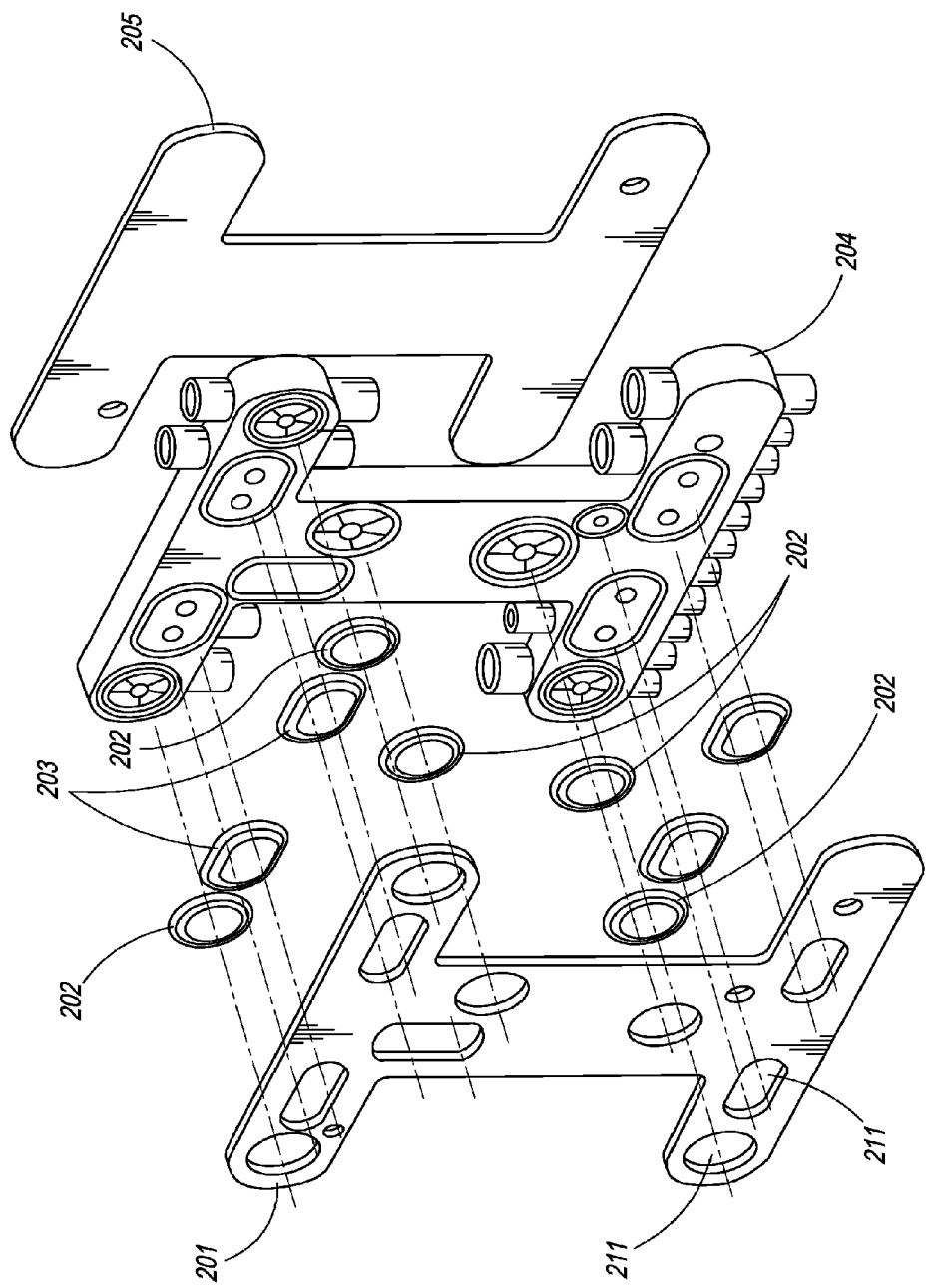
FIG. 2 illustrates the structural elements of an exemplary compact manifold, according to one embodiment of the present invention.

FIG. 2 illustrates the structural elements of the compact manifold, according to one embodiment of the present invention. The disposable manifold pumps and directs fluid flow while measuring pressure in key areas. Those fluids include blood, dialysate, infusate and anticoagulant. In addition, the manifold provides features for detecting blood leakage from the dialyzer, detecting occlusion in the arterial line, and detecting air in venous line.

Referring to FIG. 2, in one embodiment, the compact manifold 200 comprises a plurality of plastic layers with components fixedly attached therein. More specifically, the manifold 200 comprises the following elements:
Back Cover 201
Pressure Transducer Membranes 202
Valve Membranes 203
Mid Body 204
Front Cover 205
Pump tube segments (not shown in FIG. 2)

The mid-body layer 204 contains molded in channels on one side. These channels are completed by the front cover layer which is fixedly attached to the mid-body by any number of methods, including ultrasonic welding. This combined front cover-mid-body structure forms the major part of the fluid pathways within the manifold. On the opposite side of the mid-body 204 there are features that form surfaces for valving and pressure sensing, which communicate to the fluid pathways on the front cover side of the manifold. The manifold includes elastomeric components for valving and pressure sensing. These elastomeric components are captured between the back cover layer and mid-body layer through the use of ultrasonic welding and complete the fluid pathways throughout the manifold.

Referring to FIG. 2, in one embodiment, the manifold 200 comprises five pressure transducer membranes 202 and three to four membranes 203 for two-way valves. In one embodiment, the two covers 201 and 205, and mid body 204 of the manifold 200 are molded of a polycarbonate material or ABS (acrylonitrile butadiene styrene). The pressure transducer membranes 202 and valve membranes 203 are molded of a common material, such as Santoprene, or more preferably Sarlink, which is a medical grade elastomeric polymer. In one embodiment front and back covers 205 and 201 may be molded of optically clear material, at least transparent to certain preselected wavelengths of light, to allow for spectroscopic analysis of the fluid(s) contained within.

Additionally, the manifold preferably includes four pumping components. These pumping components are segments of extruded PVC tubing formulated and dimensioned to have properties optimized for pump use, particularly roller pump use. This tubing is bonded to barbed fittings that are integrally molded to the manifold mid-body. One of the four pumping components is for drawing blood from the patient's artery and pumping it through a dialyzer and back to the patient's vein. Two pumping components are for dialysate flow and one is for infusate delivery to the dialysate fluid circuit. A separate syringe pump can be used for pumping anticoagulant into the arterial blood pathway, pre-dialyzer.

In one embodiment, the manifold further incorporates tubing ports, preferably in the range of 10-14 and more preferably 12 ports, for connecting all the fluid pathways within the manifold to other components in the disposable set including dialyzer, sorbent cartridge, bag reservoir, infusate container, patient blood lines, anticoagulant, sensors, priming line and drain, as further discussed below.

In one embodiment, the manifold is shaped like a capital "I", with a first segment and a second segment parallel to each other and a connecting segment that a) is perpendicular to the first segment and second segment and b) serves to connect the first and second segments. In one embodiment, the connecting segment connects the middle of the first segment to the middle of the second segment, thereby making the distance between the connecting segment and each end of the first and second segments equidistant. It should be appreciated that the connecting segment can be placed at the ends of the first and second segment, thereby making a capital "C" or backwards "C". The manifold can also be rotated relative to the dialysis system and need not be positioned as a capital "I", e.g. it can be positioned on its side or at an angle. As shown in FIG. 3b, in an exemplary embodiment, the manifold has dimensions as follows: L1 and L2 are in the range of 4 to 7 inches, and preferably approximately 5.7 inches, L3 and L4 are in the range of 0.5 to 1.5 inches, and preferably approximately 1 inch, L5 is in the range of 2.5 to 4.5 inches, and preferably approximately 3.5 inches, and L6 is in the range of 1 to 3 inches, and preferably approximately 1.8 inches. While dimensions have been provided, it should be appreciated that the inventions disclosed herein are not limited to any specific dimension, or set of dimensions.

In one embodiment, the assembly process of the manifold 200 comprises mating the back cover 201 to the mid body 204 while affixing the membranes 202 and 203 into place by having a first side of the membranes physically attach or touch the mid body and having a second side of the membranes pass through holes, spaces, or voids 211 in the back cover 201. Preferably, the second side of the membranes have a tiered structure which permits a first tier to pass through the void 211 while the second tier remains between the back cover 201 and mid body 204. This affixes the membranes 202, 203 into the back cover 201. Furthermore, it is preferred for the mid body 204 to contain recesses into which the first side of the membranes 202, 203 rest, thereby affixing them to the mid body 204. In an alternate configuration, the membranes 202 and 203 may be co-molded to the back cover 201 in a multi-shot molding process.

One of ordinary skill in the art would appreciate that the various components of the manifold can be bound or affixed together using any suitable means. In one embodiment, the seal between the midbody and back cover is achieved via ultrasonic welding or adhesive. Alternately laser welding may be employed. The front cover is bonded to the other side of the mid body in a similar manner. Pump tubing segments are solvent bonded into place in one embodiment, or in an alternate embodiment, the segments may be laser welded using a laser absorbing additive in the plastic.

In one embodiment, the front cover is molded from BASF Terlux 2802HD, ABS, which is clear and will provide visibility to the fluid pathway. The clarity of the ABS will also provide a means for inspecting the integrity of the ultrasonically welded surfaces. ABS is preferred for its biocompatibility as well as compatibility to ultrasonic welding. Additionally, the front cover can include a molded in textured surface to help facilitate a better bond between the front cover and the mid-body. This textured surface is a chemical etching process that is known to persons of ordinary skill in the art. One preferred texture depth is 0.0045". Other suitable textures can be laser etched as well. The surface to be welded on the front cover is designed with a 0.003" recess which translates to a 0.003" raised surface on the mold. This provides an accurate surface to receive the texturing. Once the texturing takes place on the mold, the height of this 0.003" surface is lowered. Because of the peaks and valleys of the 0.0045" texture depth it is assumed that the average would be half that amount or 0.00225". The result would leave the mold in a steel safe condition of 0.00075".

In one embodiment, the front cover provides blood flow directors in both the arterial and venous pathways. These features are designed to minimize hemolysis. The blood flow directors provide for a consistent cross-sectional area throughout the pathway and minimize sharp edges to which the blood would come in contact without their presence. The wall on the opposite side of the blood flow directors has been relieved to provide a more consistent wall thickness in the molded plastic part. This will prevent sinks in this area, which could affect the surrounding welded surfaces. In one embodiment, the front cover wall thickness is 0.075".

Optionally, the front cover has alignment holes are provided for assembly purposes to ensure that the front cover and mid-body are accurately aligned during the ultrasonic welding process. The raised bosses around the alignment holes help maximize contact with the alignment pins of the welding fixture so that the plastic does not melt as easily due to friction. These bosses do not touch and are not welded to the mid-body to ensure that the hole is patent.

Figure 3A:
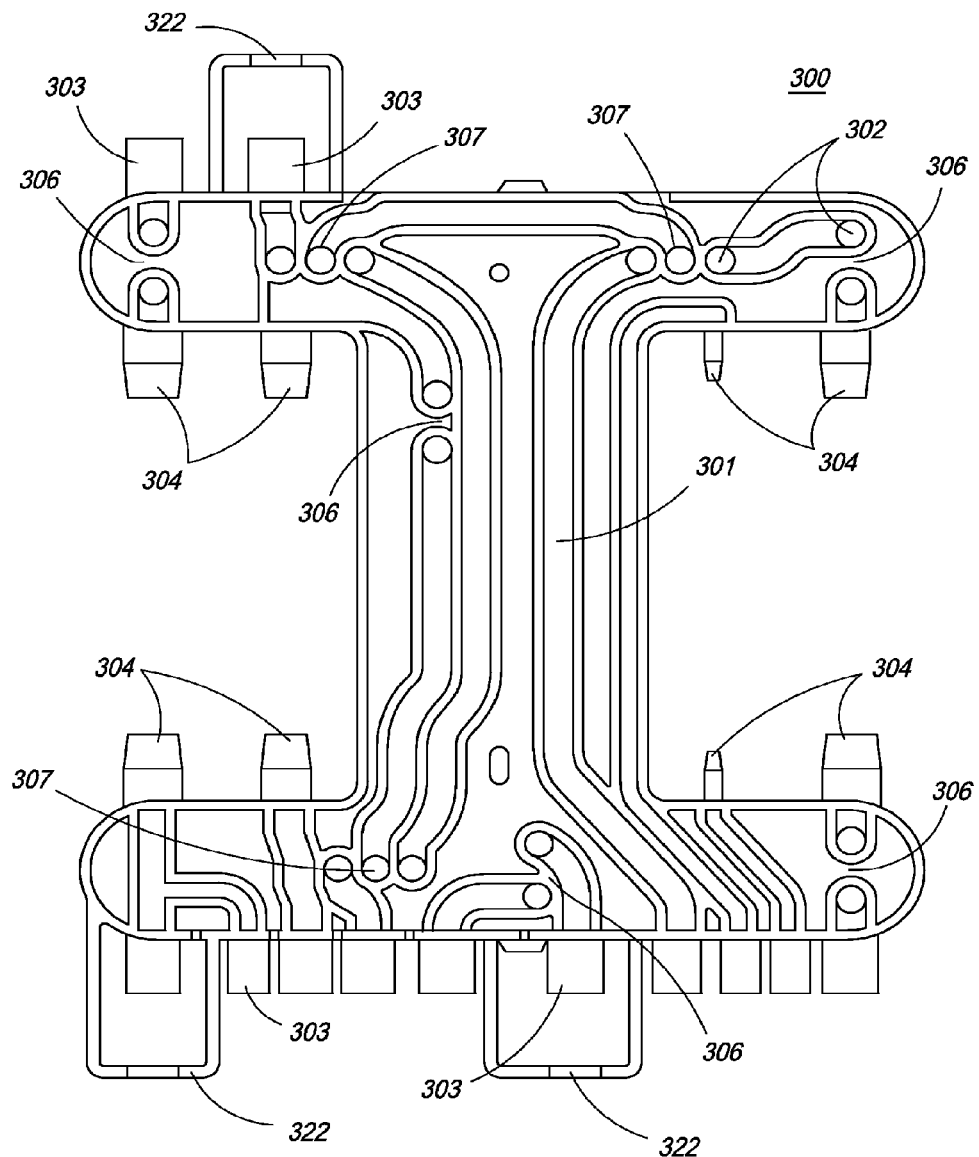
FIG. 3a provides a perspective view of the mid body component of the compact manifold.
Figure 3B:
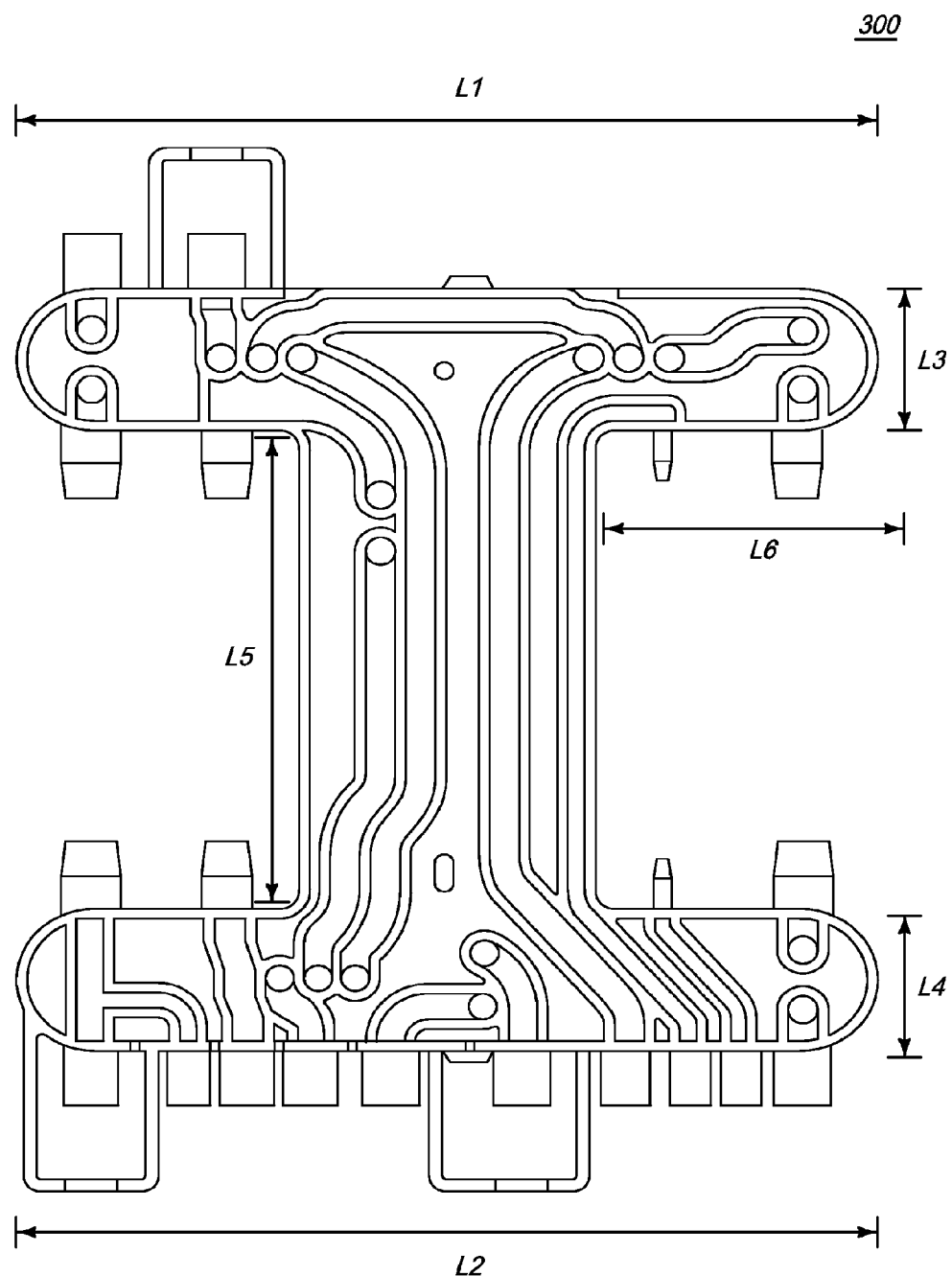
FIG. 3b provides a perspective view of the mid body component of the compact manifold with exemplary dimensions.

FIG. 3a provides a perspective view of the mid body component of the compact manifold of the present invention. As is shown in FIG. 3, the complete blood and dialysate flow paths 301 of the hemodialysis/hemofiltration system are molded into the mid body. Accommodations for the various functional elements 302 of the blood purification system, such as pumps, valves and sensors are also integrated into the mid body section of the compact manifold.

The mid-body can be molded from BASF Terlux 2802HD, ABS. Another alternative ABS is Lustran 348, White. ABS was chosen for its biocompatibility as well as compatibility to ultrasonic welding. The mid-body along with the front cover provides the fluid path channels for the manifold. The mid-body contains the energy directors for the butt joint style ultrasonic welding. In one embodiment, the energy director's dimensions are 0.019" tall with a 0.024" wide base. This results in a cross-sectional area of 0.00023 square inches. The width of the welding surface is 0.075" resulting in a weld volume of about 0.003"×0.075". A butt joint style energy director is preferred over other styles, like shear joints, tongue and groove, step joint, due to its simplicity and ability to control the molded part geometry. Vents are provided in the weld geometry to prevent trapped gases from being forced through the welds resulting in a poor weld that may leak.

The back cover side of the mid-body preferably provides a molded in textured surface to help facilitate a better bond between the back cover and the mid-body. This textured surface is a chemical etching process that is known to persons of ordinary skill in the art. The preferred texture depth is 0.0045". Other suitable textures can be laser etched as well. The surface to be welded on the mid-body is designed with a 0.003" recess which translates to a 0.003" raised surface on the mold. Once the texturing takes place on the mold, the height of this 0.003" surface is lowered. Because of the peaks and valleys of the 0.0045" texture depth it is assumed that the average would be half that amount or 0.00225". The result would leave the mold in a steel safe condition of 0.00075".

The size of the components being welded can have a major impact on the successfulness of the ultrasonic welding process. The larger the surface area, the more difficult the welding process. It is important that the welding surfaces are accurately controlled. Consistent thickness in the front and back covers is more important than flatness because a cover that is off slightly on flatness will be pressed flat during the welding process. Flatness on the mid-body is important due to the structural design that would prevent it from being flattened during the welding process. Due to these issues it is very important that the parts are designed correctly and not prone to anomalies like warpage, sinks, dimensional variations, etc. In addition, the mold construction and quality needs to match high standards that the parts will need to meet. It would follow that the molding process controls would require the highest of standards as well.

The back cover can be molded from BASF Terlux 2802HD, ABS. The back cover contains the energy directors for the butt joint style ultrasonic welding. The energy director's dimensions are 0.019" tall with a 0.024" wide base. This results in a cross-sectional area of 0.00023 square inches. The width of the welding surface is 0.075" resulting in a weld volume of about 0.003"×0.075". This 0.003" weld volume should be considered when determining the geometry of the assembled components. Vents are provided in the weld geometry to prevent trapped gases from being forced through the welds resulting in a poor weld that may leak. The alignment holes in the back cover are provided for assembly purposes to ensure that the back cover is accurately aligned to the mid-body during the ultrasonic welding process. The alignment holes in the back cover also provide accurate alignment of the manifold and instrument when properly loaded. The raised bosses around the alignment holes are designed to maximize contact with the alignment pins of the welding fixture so that the plastic does not melt as easily due to friction. These bosses do not touch and are not welded to ensure that the hole is patent.

Ultrasonic welding was chosen as the method for bonding the manifolds three major components because of the low cost of this manufacturing process. The relatively low equipment costs and cycle times to create the weld attribute to this lower manufacturing cost. Once the parts are loaded into the fixture, the welding cycle with horn travel and removal, can be accomplished in seconds. The actual weld time is about one second. Other bonding methods include hot plate, laser, and UV adhesive.

Referring to FIG. 3a, in one embodiment, the mid body section 300 has integrated within it three 2-way valves 307, five pressure transducers 306, an occlusion detector, an air bubble detector and a blood leak detector. One of ordinary skill in the art would appreciate that the number and type of functional components that are integrated within the mid body section 300 may be varied according to the requirement and application of the blood purification system and, therefore, can include 1, 2, 3, 4, 6, 7, 8, 9, 10 or more pressure transducers, 1, 2, 4, 5, 6, or more 2-way valves, 0, 2, 3, 4, or more occlusion detectors, 0, 2, 3, 4, or more air bubble detectors, 0, 2, 3, 4 or more blood leak detectors. Additionally, the mid body section 300 comprises a plurality of ports 303, 304.

The ports include internal ports 304 through which fluid flows via pump segments (not shown) from and between the first and second segments of the manifold 300. In one embodiment, the first segment has four internal ports 304, two on each side of the point where the first segment and connecting segment connect. It should be appreciated that the first segment can have 1, 2, 3, 5, 6, 7, or more internal ports. In one embodiment, the second segment has four internal ports 304, two on each side of the point where the first segment and connecting segment connect. It should be appreciated that the second segment can have 1, 2, 3, 5, 6, 7, or more internal ports. Additionally, it is preferred that the position and location of the internal ports of the first segment mirrors the position and location of the internal ports of the second segment. The ports also include external ports 303 to elements external to the manifold 300. In one embodiment, the first segment has two external ports 303. In one embodiment, the second segment has ten external ports 304. In one embodiment, the first segment has 1, 3, 4, 5, 6, 7, 8, 9, 10, 11, 12, 13, 14, 15, or more external ports 303. In one embodiment, the second segment has 1, 2, 3, 4, 5, 6, 7, 8, 9, 11, 12, 13, 14, 15, or more external ports 304.

Incorporating fluid contacting elements into the manifold, as described above, enables the design of systems where reusable sensors are mounted in the dialysis machine to which the manifold is mated while necessarily disposable fluid contacting elements are separated out and placed in the manifold, as described above. To ensure proper readings and measurements are made, the fluid contacting elements and reusable sensors need to be aligned. Mating and alignment between the manifold and dialysis machine is critical with respect to positioning and pressure applied. Typically such mating precision must provide for 0.001" to 0.010" tolerance in X, Y and Z directions and apply a mounting force in the range of 10-100 PSI to oppose fluid forces with the manifold. Such critical positioning is accomplished by means of specially designed positioning surfaces on the manifold registering with complimentary positioning surfaces on the dialysis machine. Required forces are delivered by analysis and design of dialysis machine structure to allow for X and Y positions and Z direction deflections of less than about 0.001" to 0.010" under all fluidic and mechanical pressures developed within the manifold during operation. Because the manifold contains many structures on one monolithic substrate such critical alignment need only be done once serving to position all features of the manifold with all mating features of the dialysis machine.

Figure 9:
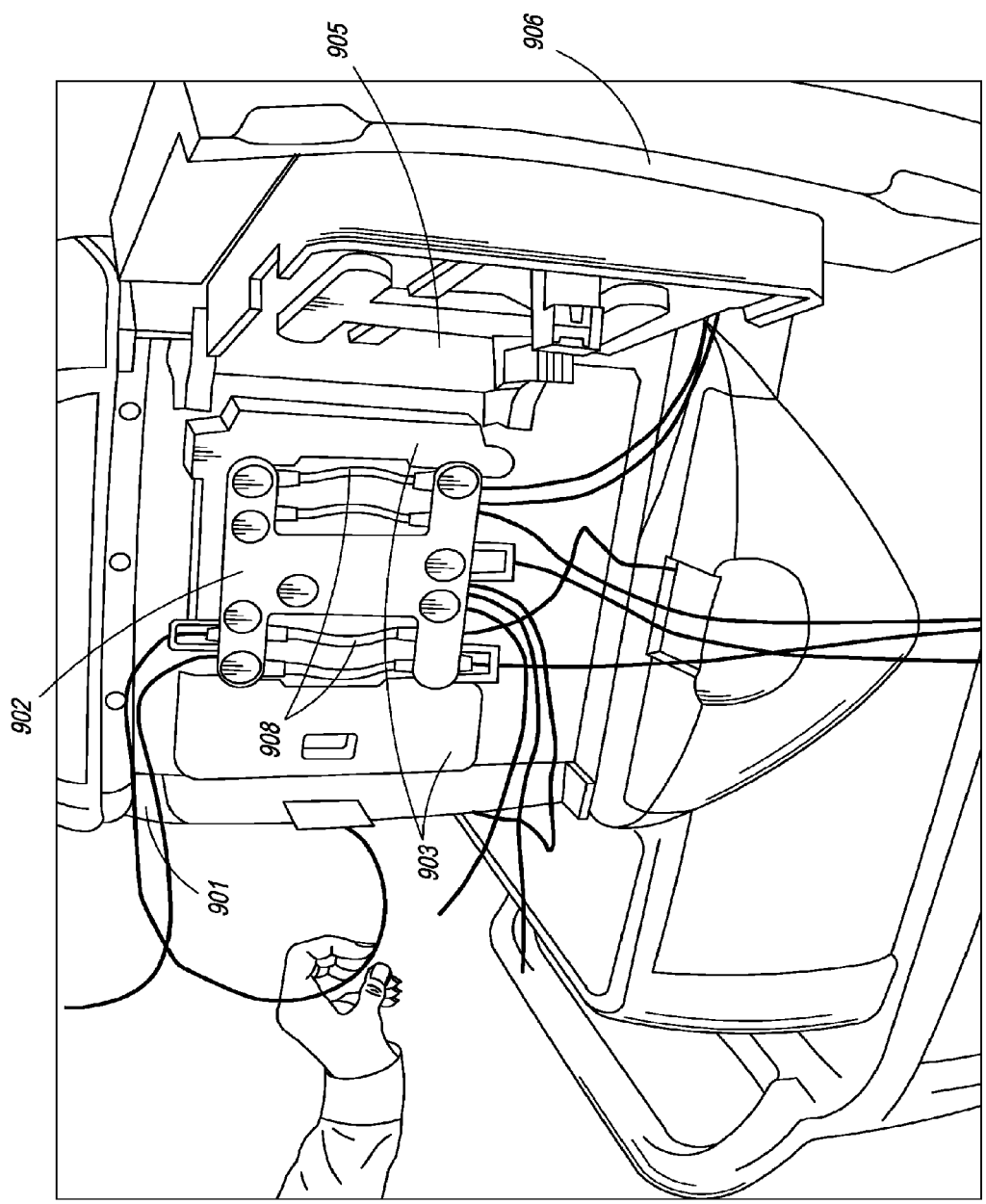
FIG. 9 shows another view of a portable dialysis system, with the manifold successfully installed.

Referring to FIG. 9, in one embodiment, the manifold 902 is mounted on the vertical front panel 903 of the dialysis system 901. The manifold is accurately located on this panel 903 by a plurality of alignment mechanisms. The first alignment mechanism comprises a plurality of alignment pins in the panel 903 that engage alignment holes in the manifold 902. The second alignment mechanism comprises at least one latch that maintains the manifold 903 in a specific mounted position until the door 906 is closed and the final accurate position is obtained. In one embodiment, the back cover of the manifold has two designed-in tabs at top and bottom. These tabs latch the manifold in a first holding position prior to the door closure and subsequent placement of the manifold's accurate position. The tabs enable a latching mechanism that can be manually released or by ball detents that require forcibly removing the manifold by hand. In another embodiment, the latch mechanism comprises a spring loaded insertion and release mechanism at the top of the back cover. This mechanism had a connecting rod between the top latch and a bottom latch. When the release mechanism at the top was activated the bottom latch released as well.

The third alignment mechanism comprises contoured guides 908 that direct the general position and configuration of the manifold 902. The contoured guides 908 are preferably shaped to mate with, match, or otherwise complement the physical structure of the manifold 902. In one embodiment, the guides 908 are generally rectangular and configured to fit inside the space bounded by the sides of the first segment, second segment, and connecting segment. The fourth alignment mechanism comprises a door 906 having at least one spring loaded pressure plate 905 that captures the manifold 902 between the door 906 and front panel 903, thereby applying adequate pressure for valving and pressure sensing. The door 906 also includes four pressure shoes that apply adequate pressure to the pumping components for rotary peristaltic delivery of fluids. It should be appreciated that one or more of the alignment mechanisms can be used, either alone or in combination, to achieve the requisite aligned and pressurized position for the manifold. It should further be appreciated that the alignment mechanisms are attached to the surface of a recessed region within the dialysis device enclosure. The recessed region comprises the front panel 903 that is recessed relative to the dialysis device housing and is bounded by four walls (a first wall, a second wall, a third and a fourth wall) that extends upward from the front panel 903 to meet and fixedly attach to the dialysis device enclosure. The recess is sufficiently deep and configured to receive the door 906.

The mid-body channel size is nominally in the range of 0.190" deep by 0.190" wide with 0.020" radiuses at the bottom corners of the channel on the mid-body side. The radius at the bottom corners of the channel should be the maximum to prevent sinks from occurring under the channel walls. These channel walls have valve and pressure diaphragm geometry on the opposite side of the mid-body, which could be adversely affected by sink in these areas. In one embodiment, the fluid pathways are square. General design rule to prevent sink is that the wall thickness of a rib (channel wall in this case) should not be more than 50-60% of the adjacent wall, to which it is attached. The channel wall is 0.075" and the adjacent wall (main manifold structure) is 0.130" resulting in 58%. The 0.190"×0.190" dialysate channels transition to the 0.155" tubing port through holes. This minimizes the accuracy required to align the front cover to the mid-body and minimizes the potential for sinks created by the thicker walls which could affect sealing features on the opposite side of the mid-body. The same approach was taken for anticoagulant and infusate channels. Gentle curves are designed into the channels to maximize laminar flow and minimize turbulent flow. In one embodiment, the Anticoagulant and infusate channels, as discussed below, measure 0.190" deep by 0.100" wide.

In one embodiment, the mid-body has alignment holes for assembly purposes to ensure that both the front cover and back cover are accurately aligned to the mid-body during the ultrasonic welding process. The raised bosses around the alignment holes maximize contact with the alignment pins of the welding fixture so that the plastic does not melt as easily due to friction. These bosses do not touch and are not welded to ensure that the hole is patent.

Figure 4:
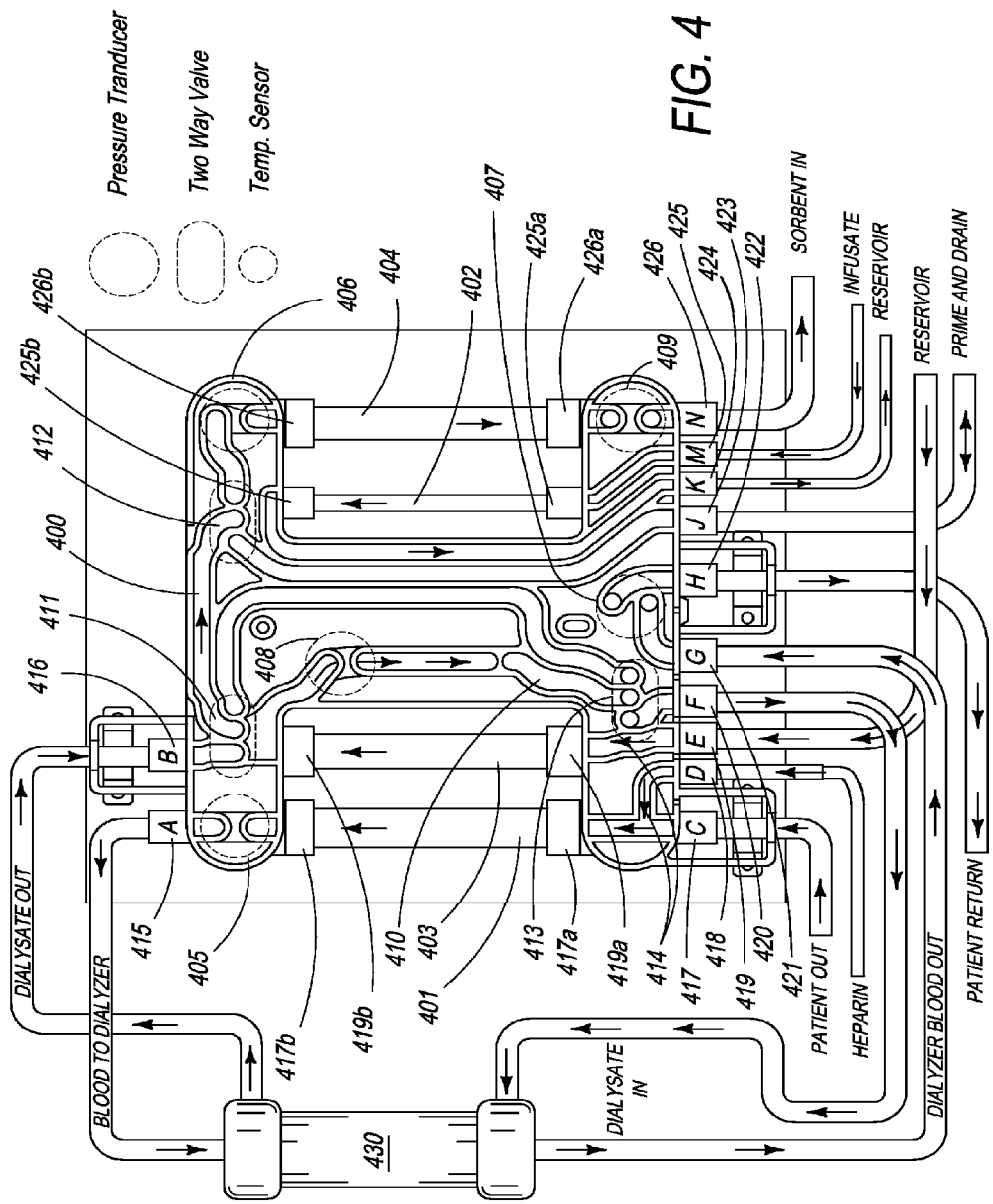
FIG. 4 is a diagram detailing the fluidic circuit for the compact manifold according to one embodiment of the present invention.

FIG. 4 is a diagram detailing the fluidic circuit for the compact manifold according to one embodiment of the present invention. The fluidic circuit comprises four peristaltic pumps P1 401, P2 402, P3 403 and P4 404. It further comprises five pressure transducers S1 405, S2 406, S3 407, S4 408 and S5 409, and a temperature sensor S6 410. In the embodiment illustrated in FIG. 4, three pairs of valves—V1A and V1B 411, V2A and V2B 412 and V3A and V3B 413 are integrated into the manifold. Grouped in this manner the pairs of six one way valves, 411 A,B, 412 A,B, 413 A,B form three two way valve assemblies 411, 412, 413.

Pump tube segments 401, 402, 403, 404 are bonded into the compact manifold. A number of ports are provided in the manifold, which connect with tubes external to the manifold to allow the flow of various fluids in and out of the manifold. These ports are connected to various tubes in the blood purification system for carrying fluids as follows:

Port A 415—blood to the dialyzer 430,
Port B 416—dialyzer output (used dialysate);
Port C 417—blood from the patient;
Port D 418—heparin for mixing in the blood;
Port E 419—reservoir output (fresh dialysate);
Port F 420—dialyzer input (fresh dialysate);
Port G 421—dialyzer output (blood);
Port H 422—patient return (clean blood);
Port J 423—connects to prime and drain line;
Port K 424—reservoir infusate input;
Port M 425—infusate in from infusate reservoir;
Port N 426—dialysate flow into sorbent.

In one embodiment, a tube segment, formed as a pathway molded into the manifold structure 400, connects the fluid flow of heparin, entering via Port D 418, to the fluid flow of blood, entering via Port C 417. The combined heparin and blood flow through port 417*a*, via pump 401, and into port 417*b* of the manifold 400. A pressure transducer is in physical communication with a tube segment, formed as a pathway molded into the manifold structure 400, which, in turn, passes the blood and heparin fluid through Port A 415. Fluid flow out of the manifold 400 at Port A 415 passes through dialyzer 430, which is external to the manifold 400. The dialyzed blood passes back into the manifold 400 through Port G 421 and into a tube segment, formed as a pathway molded into the manifold structure 400, that is in physical communication with pressure transducer 407. Fluid then passes from the tube segment through Port H 422 and into a patient return line.

Separately, dialysis fluid enters the manifold 400 from a reservoir via Port E 419. Fluid in the reservoir has infusate in it, which enters the manifold 400 via Port M 425, passes through a tube segment, formed as a pathway molded into the manifold structure 400, through another port 425*a*, through a pump 402, and back into the manifold 400 via port 425*b*. The infusate passes through a tube segment, formed as a pathway molded into the manifold structure 400, and out the manifold 400 at Port K 424, where it passes into the reservoir. The dialysis fluid which entered the manifold via Port E 419, passes through a tube segment, formed as a pathway molded into the manifold structure 400, through another port 419*a*, through a pump 403, and back into the manifold 400 via port 419*b*.

The dialysate fluid passes into a tube segment, formed as a pathway molded into the manifold structure 400, which is in physical communication with a pair of valves 411. A tube segment, formed as a pathway molded into the manifold structure 400, passes the dialysate fluid to another pair of valves 413. The tube segment is in physical communication with pressure transducers 408 and optional temperature sensor 410. The dialysate fluid passes out of the manifold 400 through Port F 420, and into a line that passes into the dialyzer 430.

A line out of the dialyzer 430 passes fluid back into the manifold 400 through Port B 416 and into a tube segment, formed as a pathway molded into the manifold structure 400, that is in physical communication with a first pair of valves 411, a second pair of valves 412, and a pressure transducer 406. The used dialysate fluid passes out of the manifold 400 through port 426*b*, through pump 404, and back into the manifold via port 426*a*. A tube segment in fluid communication with port 426*a* is in physical communication with pressure transducer 409 and passes fluid through Port N 426 and to a sorbent regeneration system.

The tubing ports are designed for circuit tubing 0.268"×0.175" tubing or anticoagulant and infusate tubing 0.161"×0.135". Preferably, the tubing ports are bonded with a suitable solvent.

In one embodiment, the 2-way valve operate by having valve actuators, which are mounted on the instrument, compress an elastomeric diaphragm over a volcano seal to prevent dialysate flow through its respective pathway. The volcano seal opening is approximately 0.190" diameter to match the channel geometry. The cross-sectional pathway through the interior of the valve is at least equivalent to 0.190" diameter when valves are open. When the valve is in the closed position the valve actuator and elastomeric diaphragm consume most of the fluid path space around the volcano seal minimizing the potential for air entrapment. There are raised plastic features on the mid-body that minimize dead space within the fluid path as well as help prevent diaphragm from collapsing around the center fluid path under negative pressure conditions. The elastomeric diaphragm has an o-ring feature around its perimeter that fits into a groove on the mid-body surface. The o-ring is compressed between the mid-body and back cover to form a fluid tight seal. The design provides for approximately 30% compression on the o-ring. The 2-way valves control the direction of dialysate flow through the manifold.

The mid-body contains structures that allow for fluid pressure monitoring across diaphragms through the use of sensors in the instrument. Fluid is allowed to flow from channels on the front cover side of the mid-body through inlet and outlet holes underneath the diaphragm on the back cover side. The cross-sectional pathway through the interior of the pressure sensing structure is at least equivalent to 0.190". The interior pathway is designed to minimize air entrapment while providing adequate fluid contact with the diaphragm. The elastomeric diaphragm has an o-ring feature around its perimeter that fits into a groove on the mid-body surface. The o-ring is compressed between the mid-body and back cover to form a fluid tight seal. The design provides for a 30% compression on the o-ring.

The valves and diaphragms can be made from a variety of different materials and by different processes. In one embodiment, the elastomeric components are made from silicone. In another embodiment, the elastomeric components are made from a variety of thermoplastic elastomers. Two shot molding may be used to attach the valves and diaphragms to the back cover. Two shot molding of valves and diaphragms would remove the need to individually assemble these parts into the manifold therefore reducing labor costs and improve quality of the manifold assembly.

Pumping components in the manifold design have been defined as PVC header tubing. These headers combined with rotary peristaltic pumping system of the instrument provide the flow of blood, dialysate, and infusate. The circuit tubing material for dialysate, infusate, and anticoagulant is preferably kink resistant, such as the tubing referred to as Colorite, Unichem PTN 780, (80 Å durometer) extruded by Natvar, all TEKNIplex companies. The tubing dimensions for the dialysate lines ranges from 0.268"×0.189" to 0.268"×0.175".

As mentioned above, the compact manifold for the dialysis system also includes a temperature sensor (Ref 410 of FIG. 4). In one embodiment of the PAK, the temperature sensor is located in the reservoir assembly. However, the temperature sensor may also be located outside the reservoir assembly, and in such embodiments, it can be integrated into the manifold, as shown in FIG. 4.

There are three major approaches using which temperature sensing can be integrated into the manifold. One of ordinary skill in the art would appreciate that variations are possible with each approach, without effecting any significant change in the overall design of the manifold. These approaches are discussed as follows:

High Conductivity Fluid Contact:

In high conductivity direct fluid contact approach, a metal disk is built into the wall of the manifold with a thermistor or any other suitable temperature sensor known in the art placed in contact with the disk on the dialysis machine side, and with fluid on the patient side. Fluid temperature may thus be monitored through the metal disk.

Conventionally, the temperature is monitored by placing a thermistor directly in the fluid stream. Use of metal disk for monitoring temperature in the present invention provides an advantage that contamination, and hence the need for cleaning of the thermistor is avoided.

A person of ordinary skill in the art would appreciate that a metal disk of any suitable metal, such as type 316 Stainless Steel may be used for the purpose. Further, a thermistor of any make appropriate for the current application may be employed. An exemplary thermistor is part number 10K 3A1A manufactured by BetaTherm.

In one embodiment, the metal disk is for single patient use and disposable, and the thermistor is part of the dialysis machine and is reused.

Medium Conductivity Fluid Contact:

The pressure transducer membranes (Ref 202 of FIG. 2) of the compact manifold are relatively thin and constructed of a medium thermal conductivity material. Thickness of typically 0.040" are used and can vary from 0.005" to 0.050" The thinner the material and the higher the thermal conductivity, the more accurately the pressure transducer membranes will transmit temperature of the dialysis fluid to the pressure transducer mounted inside the dialysis machine. By design they are in direct contact with the pressure transducer on the machine side and the fluid on the patient side. Placing a suitable temperature sensor inside the pressure transducer allows monitoring the fluid temperature. Certain pressure transducers known in the art already include a temperature sensor for correction of the transducer due to temperature drift. Such pressure transducers with temperature sensing feature can be used for the purpose of present application. An exemplary combination pressure—temperature sensor is model MPT40 manufactured by Micron Instruments. Employing such a combination of sensors avoids direct contact of the fluid measured and reduces the number of components in the manifold. This provides an alternative to the metal disk, as used in the previous approach.

Indirect Optical Temperature Measurement

If the plastic wall of the manifold fluid path is of limited thickness, such as approximately 0.020", then the plastic wall will equilibrate in temperature to the fluid inside the manifold. Under such conditions a non contact optical temperature measurement can be made from outside of the thinned wall, and fluid temperature within can be determined. An exemplary non contact optical temperature sensor is part number MLX90614 manufactured by Melxis. The non contact approach provides the advantage that it requires no additional parts in the manifold. The only requirement is a thin section in the fluid path walls. This approach provides low cost and still maintains single patient use safety features.

Apart from pressure transducers and temperature sensor, other sensors may also be included for integrating with the compact manifold. These other sensors include, but are not limited to, ammonia sensor, pH sensor and conductivity sensor. The ammonia and pH sensors may be integrated as individual sensors into the manifold, or as a single 'module' that comprises both the sensors.

Figure 5:
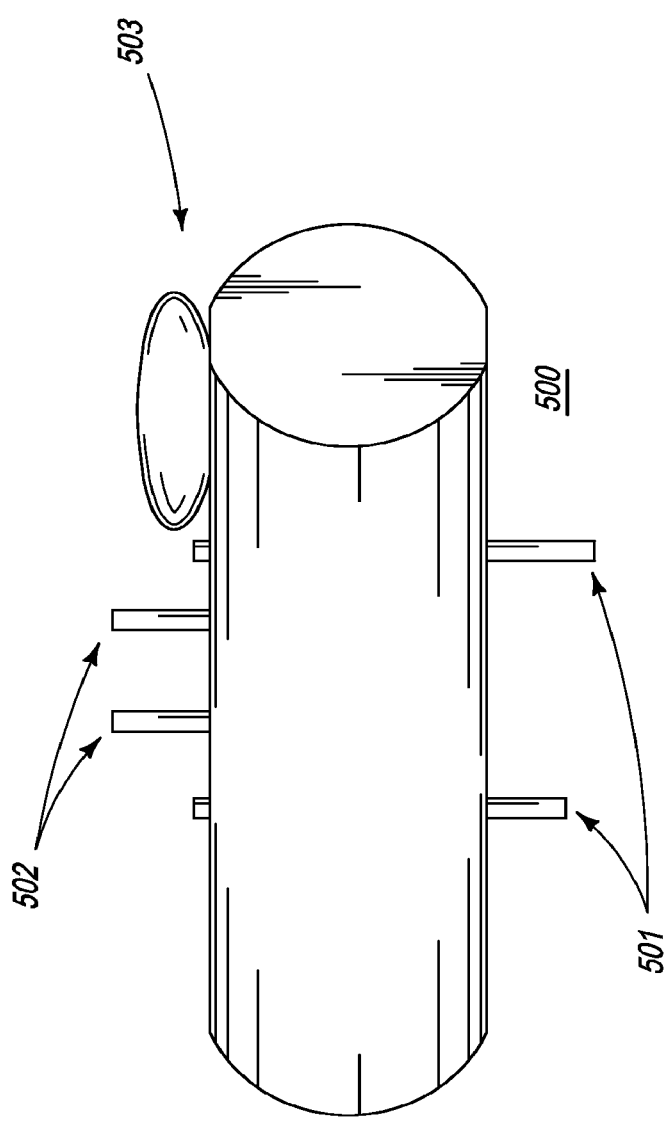
FIG. 5 illustrates an exemplary conductivity cell within the compact manifold.

One possible implementation for an integral conductivity sensor in the manifold is as a conductivity cell with electrical pins contacting the dialysate fluid. The technical details of an exemplary conductivity cell are shown in FIG. 5. Referring to FIG. 5, the conductivity cell 500 comprises bias pins 501 for applying a small, constant current to the fluid. Sensing pins 502 detect the voltage in the fluid, wherein the magnitude of the detected voltage is dependent on the conductivity and temperature of the fluid. The temperature is measured using a thermistor 503 placed next to the conductivity cell 500. Alternately the temperature can be determined by one of the means disclosed above. Knowing the values of the measured temperature and voltage at the sensing pins 502, conductivity of the fluid can be determined.

The current applied through the bias pins 501 can be DC or an AC signal and is generally in the 50-100 kHz frequency range. In one embodiment, the magnitude of the applied current is of the order of 10 mA. Sensing pins 502 are generally depth positioned during manufacture of the conductivity cell, typically to a depth of +/−0.001 inch with cal solution in the cell. The thermistor 503 has a typical accuracy of 0.5 Deg C.

The conductivity cell can be built into a dialysate fluid passage of the compact manifold by driving or molding in place conductive pins (bias pins and sensing pins) into the manifold body such that they come in contact with the dialysate but do not allow dialysate to leak out of the manifold.

In one embodiment, sensing for blood leakage, air bubbles, and/or occlusion is achieved by including optical sensors in the dialysis machine which attach to, and around, pre-defined areas of the manifold. Referring back to FIG. 3*a*, the manifold 300 comprises a plurality of tubing support brackets 322 which facilitate accurately placing the circuit tubing into optical sensors, such as Optek sensors, that are separately mounted in the instrument when the manifold is installed and the door is shut. The sensors provide means for detecting occlusion in the arterial line, blood leak in the blood line downstream of the dialyzer and air detection in the venous blood line. The brackets restrain the tubing on one side of the sensor while the tubing port does the restraining on the other side of the sensor. These optical sensors are U shaped devices into which the tubing is forced when the manifold is installed. The tubing support brackets provide support for the tubing so that all three of these sensors are loaded with the same motion as loading the manifold, with no extra effort on the user's part.

Figure 6A:
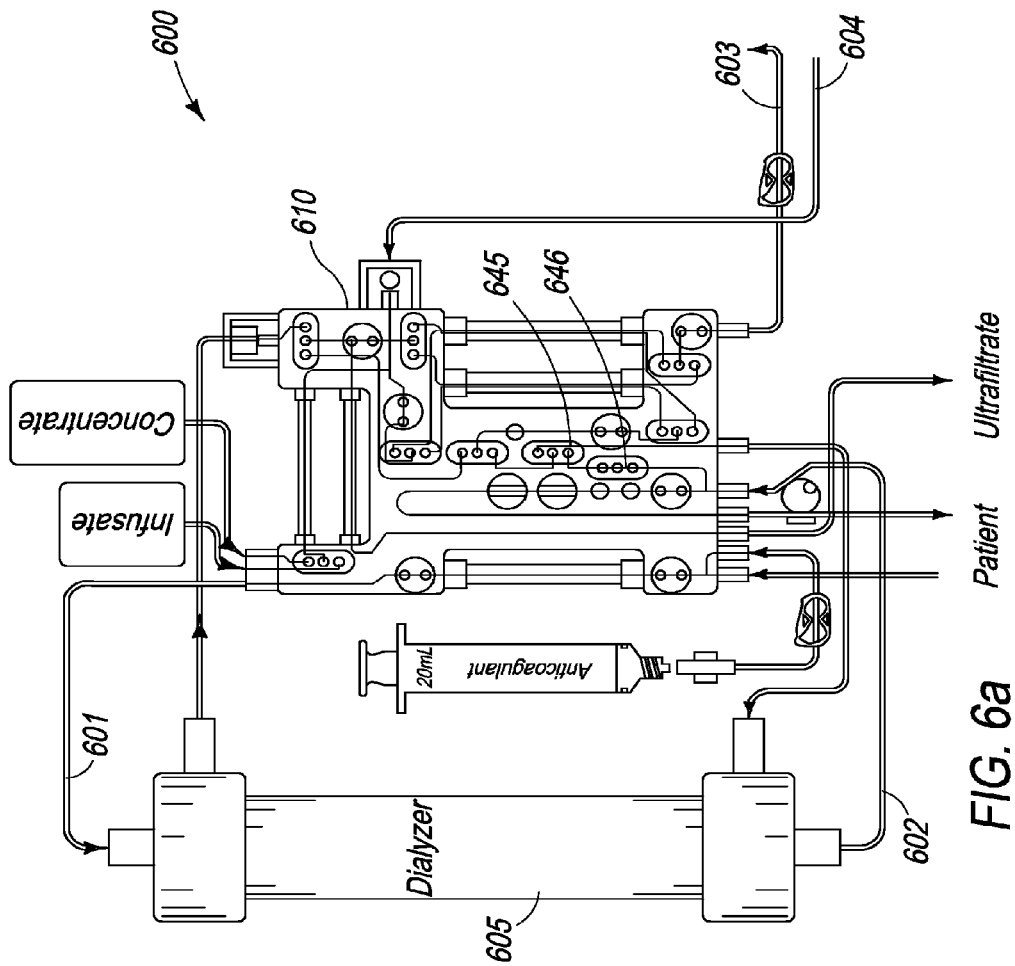
FIG. 6a shows an extracorporeal blood processing system according to one embodiment of the present invention, with two two-way valves integrated into the compact manifold that are used to determine the mode of operation of the system.

As mentioned earlier, the extracorporeal blood processing system of the present invention is implemented as a portable artificial kidney (PAK) that is capable of operating in hemodialysis or hemofiltration configuration as required. To allow the user to select the desired mode of operation (hemodialysis or hemofiltration), in one embodiment the system is provided with two-way valve(s). These valves can be actuated by a user to direct dialysate flow either through the dialyzer in one mode of operation or to deliver infusate grade dialysate flow directly to a patient, in a second mode of operation. These two-way valves can also be integrated with the compact manifold of the dialysis circuit. This is illustrated in FIG. 6*a*. It should be noted that in FIGS. 6*a* through 6*e*, for the purpose of clarity, corresponding elements have the same numbers.

Referring to FIG. 6*a*, the extracorporeal blood processing system 600 comprises a plastic molded compact manifold 610 that encapsulates a plurality of molded blood and dialysate fluidic paths as well as a plurality of sensors, valves and fluidic pumps. The dialyzer 605 when connected to the arterial blood tube 601 and venous blood tube 602 of manifold 610 completes the blood circuit of system 600. In one embodiment, the dialyzer 605 is disposable. Two lines—603 and 604, are used for circulating spent and fresh dialysate respectively. For operating the system 600 in either of the two modes (hemodialysis and hemofiltration), a two-way valve 645, and a backup two-way valve 646 are provided. Back up valve 646 is employed because the dialysate used in hemodialysis is not sterile and not infusion grade while the fluid used in hemofiltration is. In the event of operation in hemodialysis mode and a leak or other failure of valve 645, valve 646 provides double protection against that fluid being pumped into the patient blood stream. Inclusion of backup valve 646 allows the use of one manifold for both hemodialysis and hemofiltration safely. As noted above two way valves such as backup valve 646 are composed of two single valves. In this case both one way valves are in series and so by closing both ports of two way valve 646 double protection is afforded preventing dialysate from entering the blood stream. In an alternate embodiment a manifold can be made that is only intended for hemodialysis, having no connection between dialysis fluid circuit and blood circuit and valve 646 be safely eliminated.

Figure 6B:
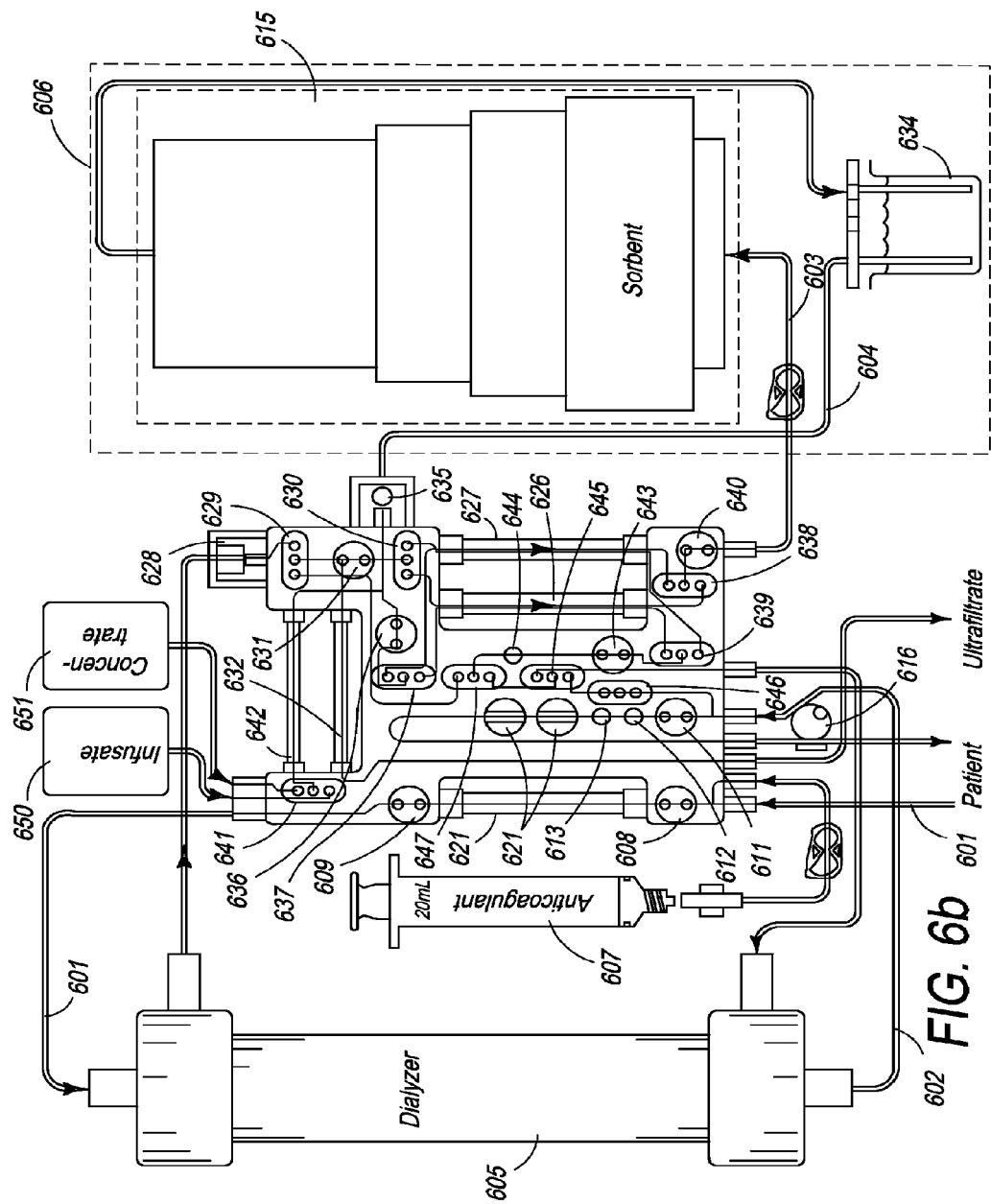
FIG. 6b illustrates in further detail, the circuit for hemodialysis/hemofiltration system according to one embodiment of the present invention.

FIG. 6*b* illustrates in further detail, the circuit for hemodialysis/hemofiltration system according to one embodiment of the present invention. Referring to FIG. 6*b*, the spent dialysate and fresh dialysate tubes 603 and 604 respectively are connected to a dialysate regeneration system 606 thereby completing the dialysate circuit of the system 600. The dialysate regeneration system 606 further comprises disposable sorbent cartridges 615 and a reservoir 634 to hold dialysate cleansed by cartridges 615. Other components of the system shown in FIG. 6*b*, and their functionality is explained with reference to FIG. 6*c*, which shows an exploded view of the extracorporeal blood processing system 600 configured to operate in hemodialysis mode. Corresponding elements in FIGS. 6*b* and 6*c* have the same numbers.

Figure 6C:
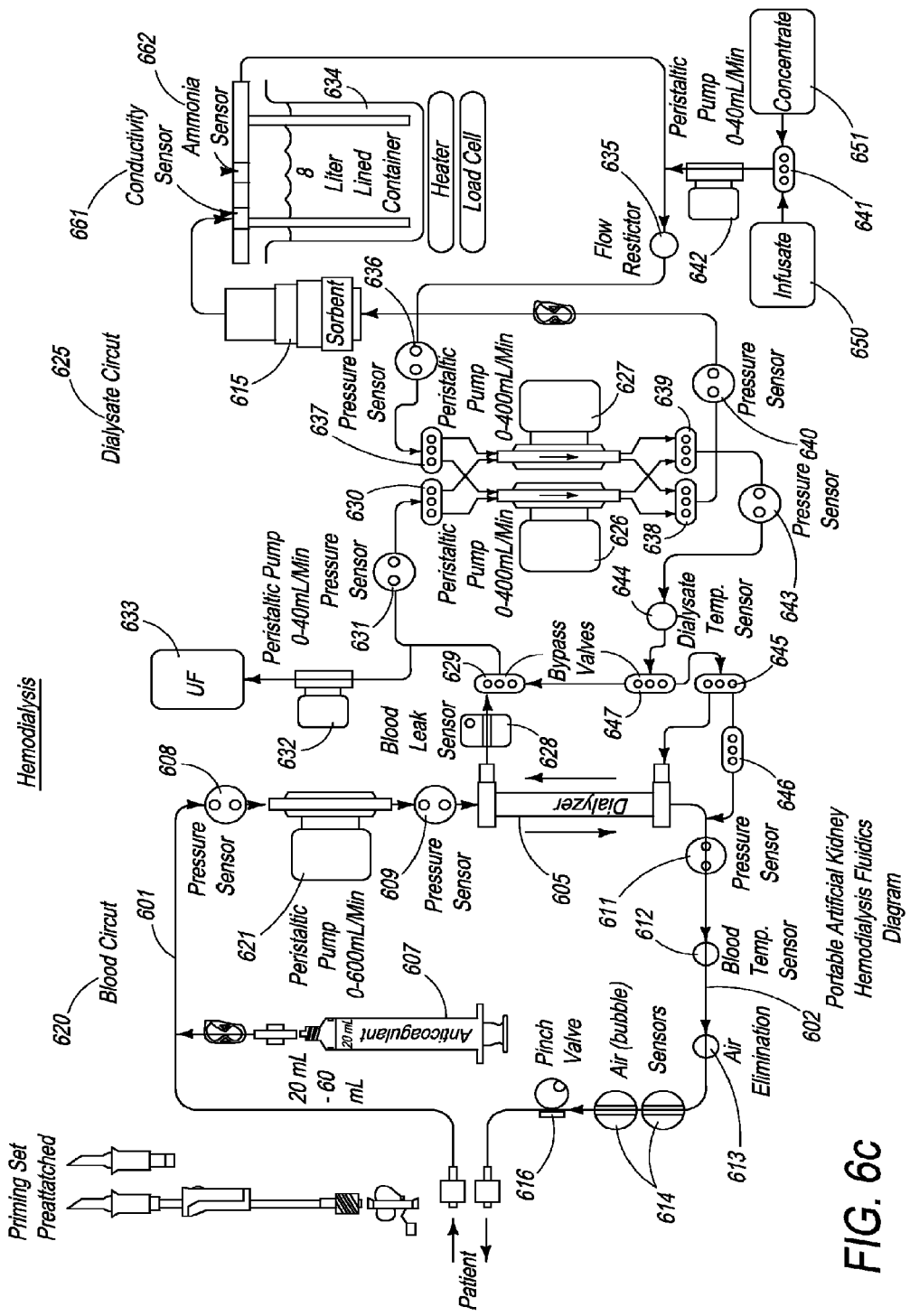
FIG. 6c shows an exploded view of the extracorporeal blood processing system of the present invention, configured to operate in hemodialysis mode.

Referring to FIGS. 6*b* and 6*c*, there are two fluid circuits—blood circuit 620 and dialysate circuit 625. Blood circuit 620 comprises a peristaltic blood pump 621 that draws a patient's arterial impure blood along the tube 601 and pumps the blood through dialyzer 605. A syringe device 607 injects an anticoagulant, such as heparin, into the drawn impure blood stream. Pressure sensor 608 is placed at the inlet of the blood pump 621 while pressure sensors 609 and 611 are placed upstream and downstream of the dialyzer 605 to monitor pressure at these vantage points. As purified blood flows downstream from the dialyzer 605 and back to the patient, a blood temperature sensor 612 is provided in the line to keep track of temperature of the purified blood. An air eliminator 613 is also provided to remove accumulated gas bubbles in the clean blood from the dialyzer. A pair of air (bubble) sensors (or optionally a single sensor) 614 and a pinch valve 616 are employed in the circuit to prevent accumulated gas from being returned to the patient.

The dialysate circuit 625 comprises two dual-channel dialysate pumps 626, 627. Dialysate pumps 626, 627 draw spent dialysate solution from the dialyzer 605 and the regenerated dialysate solution from reservoir 634 respectively. At the point where used dialysate fluid from the dialyzer 605 enters the dialysate circuit 602, a blood leak sensor 628 is provided to sense and prevent any leakage of blood into the dialysate circuit. Spent dialysate from the outlet of the dialyzer 605 then passes through the bypass valve 629 to reach two-way valve 630. A pressure sensor 631 is placed between the valves 629 and 630. An ultrafiltrate pump 632 is provided in the dialysate circuit, which is operated periodically to draw ultrafiltrate waste from the spent dialysate and store it in an ultrafiltrate bag 633, which is emptied periodically.

As mentioned previously, spent dialysate is regenerated using sorbent cartridges. The dialysate regenerated by means of sorbent cartridge 615 is collected in a reservoir 634. The reservoir 634 includes conductivity and ammonia sensors 661 and 662 respectively. From the reservoir 634, regenerated dialysate passes through flow restrictor 635 and pressure sensor 636 to reach a two-way valve 637. Depending upon patient requirement, desired quantities of infusate solution from the reservoir 650 and/or concentrate solution from the reservoir 651 may be added to the dialysis fluid. Infusate and concentrate are sterile solutions containing minerals and/or glucose that help maintain minerals like potassium and calcium in the dialysate fluid at levels prescribed by the physician. A bypass valve 641 and a peristaltic pump 642 are provided to select the desired amount of infusate and/or concentrate solution and to ensure proper flow of the solution into the cleansed dialysate emanating from the reservoir 634.

The dialysate circuit comprises two two-way valves 630 and 637. The valve 630 directs one stream of spent dialysate to a first channel of dialysate pump 626 and another stream of spent dialysate to a first channel of dialysate pump 627. Similarly, valve 637 directs one stream of regenerated dialysate to a second channel of dialysate pump 626 and another stream of regenerated dialysate to a second channel of dialysate pump 627.

Streams of spent dialysate from pumps 626 and 627 are collected by two-way valve 638 while streams of regenerated dialysate from pumps 626 and 627 are collected by two-way valve 639. The valve 638 combines the two streams of spent dialysate into a single stream that is pumped via pressure sensor 640 and through sorbent cartridges 615 where the spent dialysate is cleansed and filtered, collected in the reservoir 634. The valve 639 combines the two streams of regenerated dialysate into a single stream, which flows to the two-way valve 645 through a bypass valve 647. A pressure sensor 643 and a dialysate temperature sensor 644 are provided on the dialysate flow stream to the two-way valve 645.

By reversing the state of two way valves 630, 637, 638 and 639 the two pumps 626 and 627 are reversed in their action of one withdrawing dialysis fluid from the dialyzer 605 and the other supplying dialysis fluid to the dialyzer 605. Such reversal, when done periodically over short periods of time relative to the dialysis session, insures that over the longer period of the entire dialysis session the dialysate fluid volume pumped into the dialyzer equals the amount of fluid pumped out and the only total fluid volume lost by dialysis circuit 625 is that removed by ultrafiltrate pump 632.

In hemodialysis mode, depicted in FIG. 6c two-way valve 645 allows the regenerated dialysate to enter dialyzer 605 to enable normal hemodialysis of the patient's blood. One side of valve 645 is closed leading to the patient's blood return line. Another two-way valve 646 acts as a backup, keeping dialysate form the patient's blood line with both ports of valve 646 closed even if valve 645 leaks or fails.

Figure 6D:
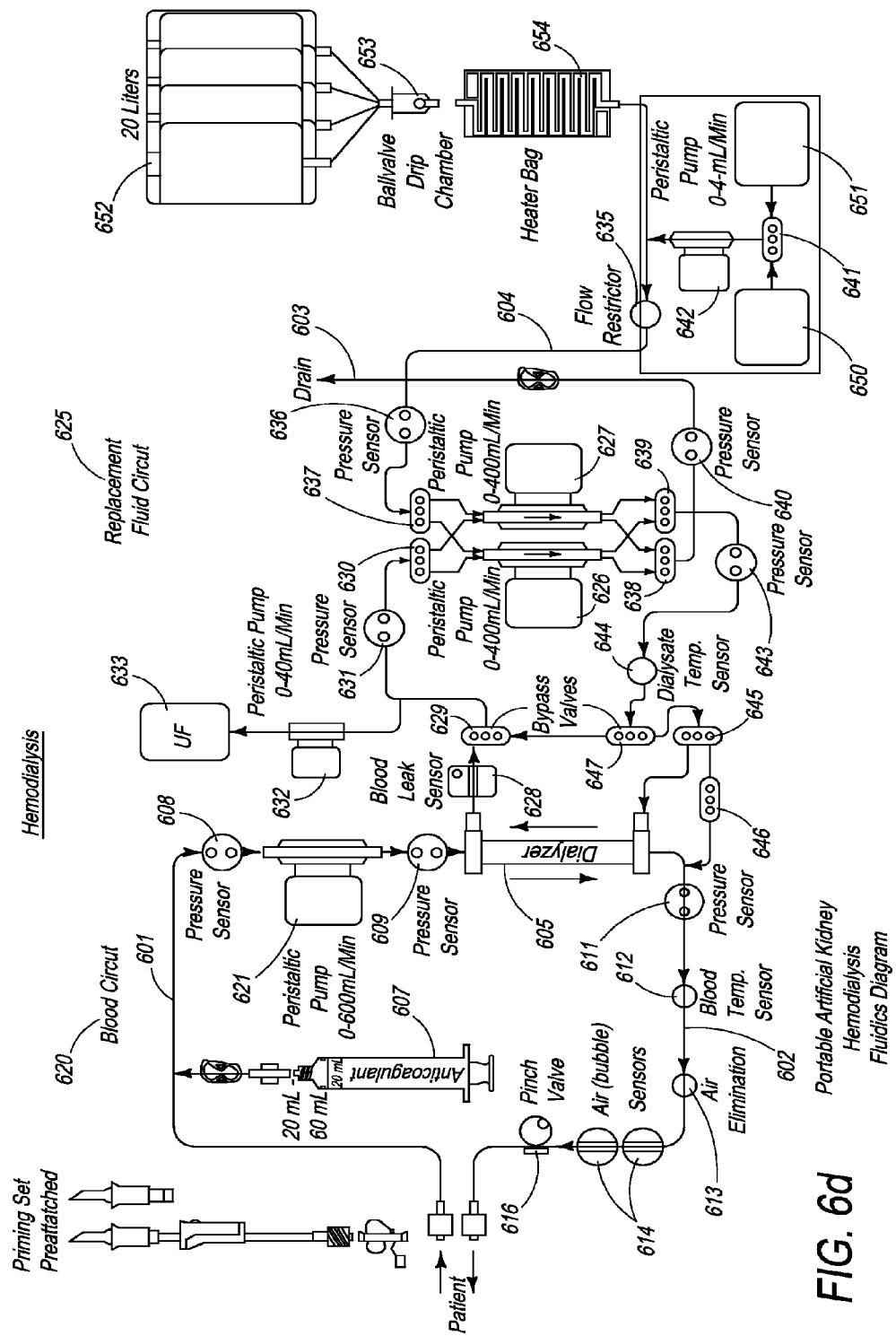
FIG. 6d illustrates an embodiment where the extracorporeal blood processing system of the present invention is configured to operate in hemofiltration protocol.

In hemofiltration mode of operation, depicted in FIG. 6d the two-way valve 645 can be actuated to direct a stream of fresh ultrapure dialysate from reservoir 652 through valve 646, now with both ports open to directly enter the stream of purified blood emanating from the dialyzer and flowing back to patient.

It should be noted by persons of ordinary skill in the art that the backup two-way valve 646 is a redundant safety valve to ensure that in hemodialysis mode failure of one valve 645 does not result in infusion of regenerated dialysate directly into the patient. That is, both the valves 645 and 646 are capable of being actuated by the user to allow fluid to be directed to the patient's venous blood line as a safety consideration. In one embodiment the two-way back-up valve 646 is a single valve to allow or stop fluid flow.

It should be further noted by persons of ordinary skill in the art that valves as described in the description above are termed as 'bypass' or 'two-way' depending upon their use. Thus, valves are termed 'bypass valves' when they bypass something like the dialyzer. Otherwise they are termed 'two-way valves' and simply direct the flow in at least two directions. However, the bypass and two-way valves are identical in construction.

In one embodiment, the two-way valves used in the present invention are fabricated as elastomeric membranes that are pressed against an orifice by a mechanism contained inside the dialysis machine to stop flow having fluid contact with the rest of the fluidic circuit.

As mentioned, two-way valves 645 and 646 can be used for changing the mode of operation for the blood processing system. FIG. 6d shows an embodiment, in which the system 600 is configured as operating in hemofiltration protocol. Referring to FIG. 6d, fluid flow in blood and dialysate circuits 620 and 625 is depicted. Since the system is operating in hemofiltration mode, therefore the spent dialysate tube 603 is connected to a drain while the fresh, dialysate tube 604 is connected to fresh ultrapure and injectable grade dialysate reservoirs 652. Fresh dialysate through a ball-valve drip chamber 653 passes through a heater bag 654 to flow into the fresh dialysate tube 604. The rest of the elements and fluidic paths of the blood and dialysate circuits 620, 625 are similar to those of FIG. 6c, except that in hemofiltration protocol fresh dialysate or replacement fluid is introduced into the dialysate circuit 625 as the spent dialysate is drained and not reused. Also depicted by grey shading in FIG. 6d in hemofiltration mode the infusate subsystem incorporating components 642, 650, 641 and 651 is unused.

Referring to FIG. 6d, the blood circuit 620 comprises a peristaltic blood pump 621 that draws a patient's arterial impure blood along tube 601 and pumps the blood through dialyzer 605. An optional pump 607 injects an anticoagulant, such as heparin, into the drawn impure blood stream. Pressure sensor 608 is placed at the inlet of the blood pump 621 while pressure sensors 609 and 611 are placed upstream and downstream of the dialyzer 605. Purified blood from the dialyzer 605 is pumped through tube 602 past a blood temperature sensor 612, air eliminator 613 and Air (bubble) sensors 614 and back to a vein of the patient. A pinch valve 616 is also placed to completely stop blood flow if air is sensed by the bubble sensor 614 in the line upstream of the pinch valve 616 thereby preventing the air from reaching the patient.

The dialysate circuit 625 comprises two dual-channel dialysate pumps 626, 627. Dialysate pumps 626, 627 draw spent dialysate solution from the dialyzer 605 and the fresh dialysate solution from reservoirs 652 respectively. Spent dialysate from the outlet of the dialyzer 605 is drawn through blood leak sensor 628 and bypass valve 629 to reach two-way valve 630. Pressure sensor 631 is placed between the valves 629 and 630. An ultrafiltrate pump 632 is operated periodically to draw ultrafiltrate waste from the spent dialysate and store in an ultrafiltrate bag 633 (that is emptied periodically). Fresh dialysate from the reservoirs 652 passes through flow restrictor 635 and pressure sensor 636 to reach two-way valve 637. Persons of ordinary skill in the art would realize that in this protocol infusate and concentrate is not needed and accordingly elements 641, 642, 650, 651 associated with those functions are shown "grayed out". In the fluidic diagram of FIG. 6e the two-way valve 641 as well as pump 642 are depicted in grey indicating that they are not in use, but are part of the common manifold 610 of FIG. 6a.

The heater bag 654 raises the temperature of the fresh dialysate sufficiently so that the temperature of the ultrafiltered blood going back to the patient from the dialyzer 605 or the overall temperature of the mixture of ultrafiltered blood from dialyzer 605 and the fresh dialysate infused directly into the purified blood by actuating the valves 645, 646 is equivalent to the body temperature of the patient thereby preventing any thermal shock.

Figure 6E:
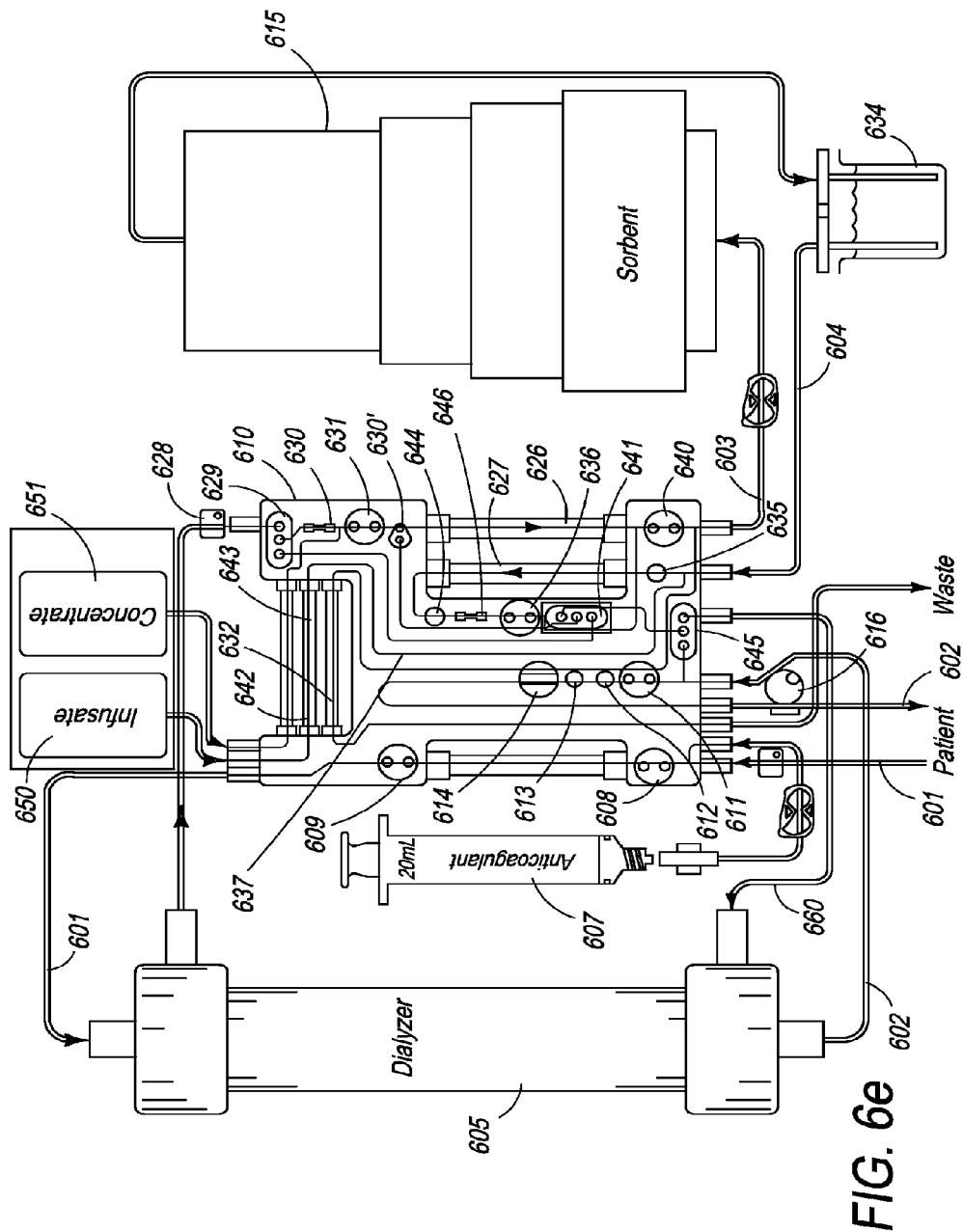
FIG. 6e shows another embodiment, where the compact manifold comprises only one two-way valve to determine the mode of operation of the system.

FIG. 6e shows an alternative embodiment of the fluidic set where the backup two-way valve 646 of FIGS. 6a through 6c is not used. Referring now to FIG. 6e, the blood circuit comprises peristaltic blood pump 621 that draws a patient's arterial impure blood along tube 601 and pumps the blood through dialyzer 605. A pump 607 injects an anticoagulant, such as heparin, into the drawn impure blood stream. Pressure sensor 608 is placed at the inlet of the blood pump while pressure sensors 609 and 611 are placed upstream and downstream of the dialyzer 605. Purified blood from the dialyzer 605 is pumped through tube 602 past a blood temperature sensor 612, air eliminator 613 and Air (bubble) sensor 614 and back to a vein of the patient. A pinch valve 616 is also placed before circuit connection to the patient to completely stop blood flow if air is sensed by the Air (bubble) sensor 614 in the line upstream of the pinch valve 616 thereby preventing the air from reaching the patient.

The dialysate circuit comprises two dialysate pumps 626, 627. Dialysate pumps 626, 627 draw spent dialysate solution from the dialyzer 605 and the regenerated dialysate solution from reservoir 634 respectively. Spent dialysate from the outlet of the dialyzer 605 is drawn through blood leak sensor 628 to reach bypass valve 629. Flow sensor 630 is one of two flow sensors (the other being flow sensor 646) which determine the volume of dialysate flowing through the circuit. Valve 630' is similar in construction to a two-way valve and is used to bypass dialysate pump 626. Valve 630' is normally closed in the direction of the bypass. In the event of stopping of the dialysate pump 626, valve 630' is opened to direct flow around pump 626. Pressure sensor 631 is placed between the flow sensor 630 and the valve 630'. During normal flow, the spent dialysate is pumped via pressure sensor 640 and through sorbent cartridges 615 where the spent dialysate is cleansed and filtered. The cleansed/filtered dialysate then enters reservoir 634. An ultrafiltrate pump 632 is operated periodically to draw ultrafiltrate waste from the spent dialysate and store in an ultrafiltrate bag (not shown) that is emptied periodically.

Regenerated dialysate from the reservoir 634 passes through flow restrictor 635, dialysate temperature sensor 644, flow sensor 646 and pressure sensor 636 to reach two-way valve 645 through bypass valve 641. When the respective flow paths of bypass valves 629 and 645 and 641 are activated they direct regenerated dialysate to bypass the dialyzer 605. Infusate and concentrate streams from infusate and concentrate reservoirs 650, 651 are directed by infusate and concentrate pumps 642, 643 into the cleansed dialysate emanating from the reservoir 634 and the spent dialysate downstream of flow sensor 630, respectively.

The two-way valve 645 determines what mode the system 600 is operating in. Thus, in one mode of operation the two-way valve 645 allows the regenerated dialysate to enter dialyzer to enable normal hemodialysis of the patient's blood. In another mode of operation, the two-way valve 645 is actuated to direct fluid flow of ultra pure infusate grade dialysis fluid into the venous blood line and directly to patient. Accordingly, the versatile valves enable the mode of operation to switch between hemofiltration and hemodialysis. For example, in hemofiltration shown in FIG. 6d infusible grade fluid is routed through the three valves directly into the blood stream where valve 646 connects to the post dialyzer. In this mode valve 645 prevents the dialysate fluid from entering the lower port of the dialyzer. In hemodialysis, shown in FIG. 6,c valve 646 is closed and valves 647 and 645 route dialysate fluid to the dialyzer.

It should be noted that while the embodiments of FIGS. 6c and 6e represent two different flow control concepts. While the embodiment of FIG. 6c uses pump swapping and a plurality of valves to control fluid volume, the embodiment of FIG. 6e uses flow sensors 630 and 646 to control fluid volume.

Figure 7:
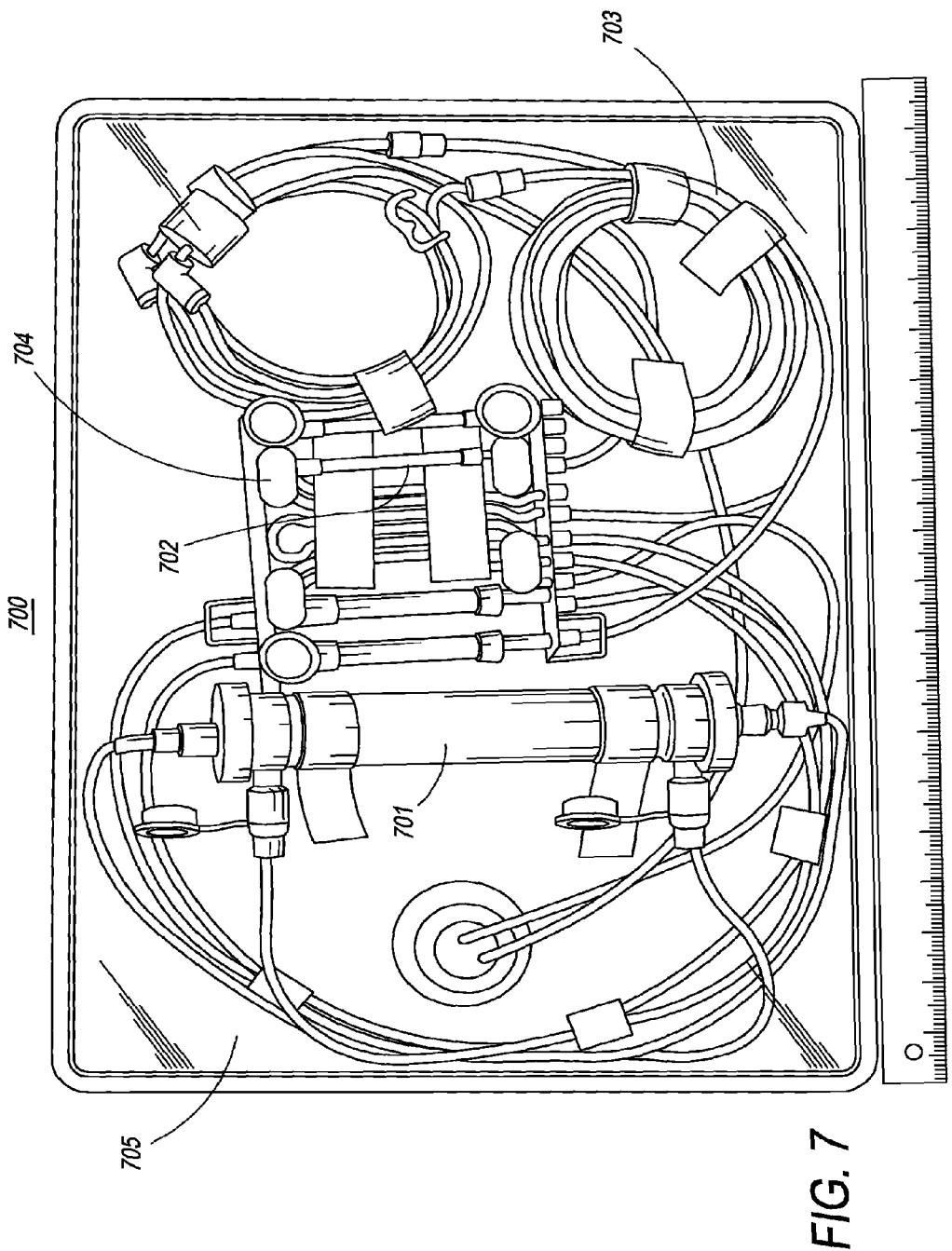
FIG. 7 illustrates an embodiment where the blood and dialysate circuits are fully disposable, preassembled with the dialyzer, and are prepackaged in a kit together with the compact manifold.

The use of a manifold for fluidic circuit of a hemodialysis system enables the dialysis unit (portable artificial kidney, or PAK) to be modular and portable, with improved functionality. The manifold can be manufactured as a separate unit that can be easily installed into the dialysis unit. FIG. 7 illustrates an embodiment where the blood and dialysate circuits are fully disposable, and are prepackaged in a kit 700. The kit includes the dialyzer 701, manifold 702, tubing 703, valves 704 (as part of the manifold), reservoir bag 705, and other disposable components.

Figure 8:
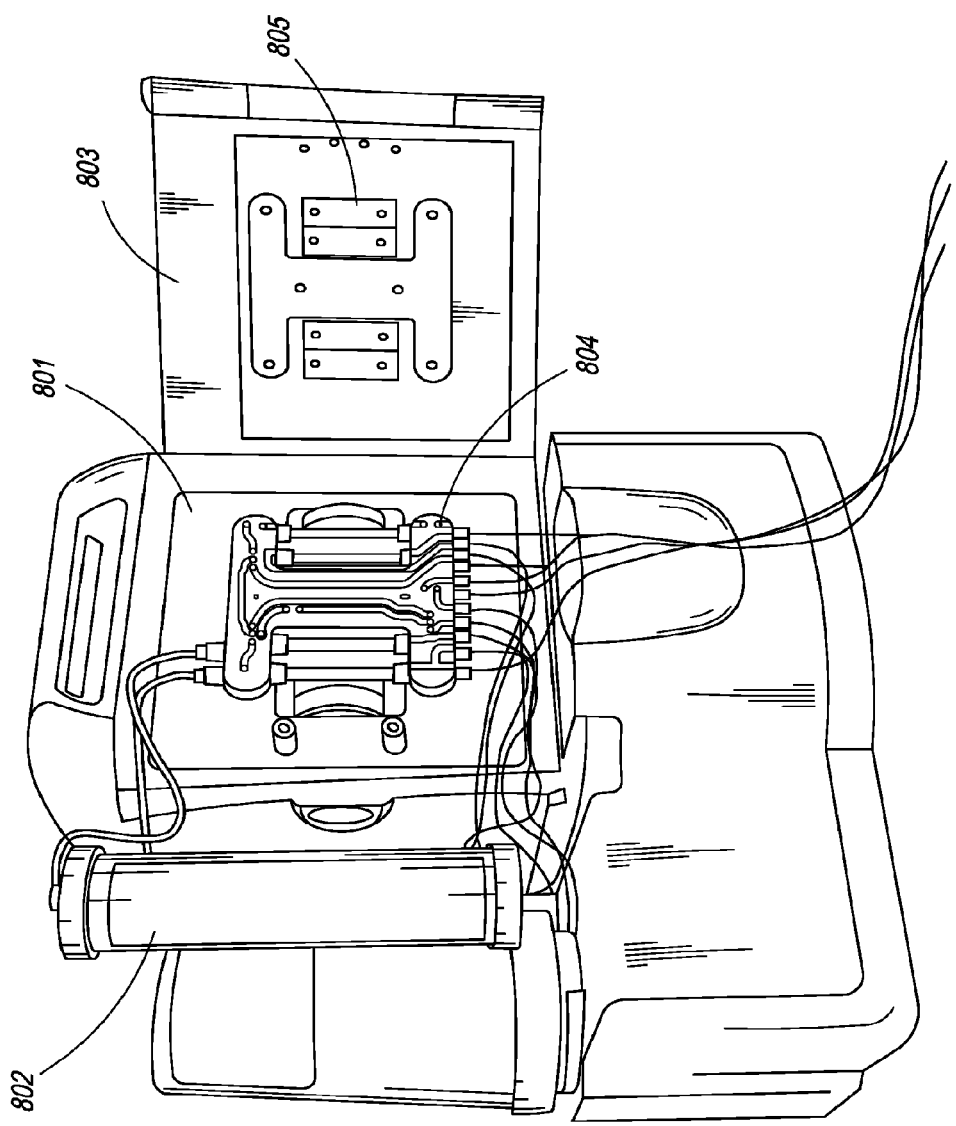
FIG. 8 illustrates the installation of the compact manifold in a portable dialysis system.

FIG. 8 illustrates the manifold as installed in the dialysis machine. Referring to FIG. 8, the dialysis machine 801 has a front door 803 which can be widely opened to install the disposable components. For installation, the manifold 804 simply needs to be inserted in the space provided for the purpose in the dialysis unit 801. Installing the dialyzer 802 also involves a simple insertion in a designated recess. The front door 803 is provided with pump shoes that makes loading of disposable components very easy, as no pump tubing needs to be thread between roller and shoes. Further, this arrangement allows installing the dialyzer 802 and the manifold 804 in a manner that ensures proper alignment against non-disposable components such as pressure readers, sensors, and other components. This packaged, simple approach enables easy disposables loading and cleaning of the system. It also ensures that the flow circuitry is properly configured and ready for use.

Figure 10:
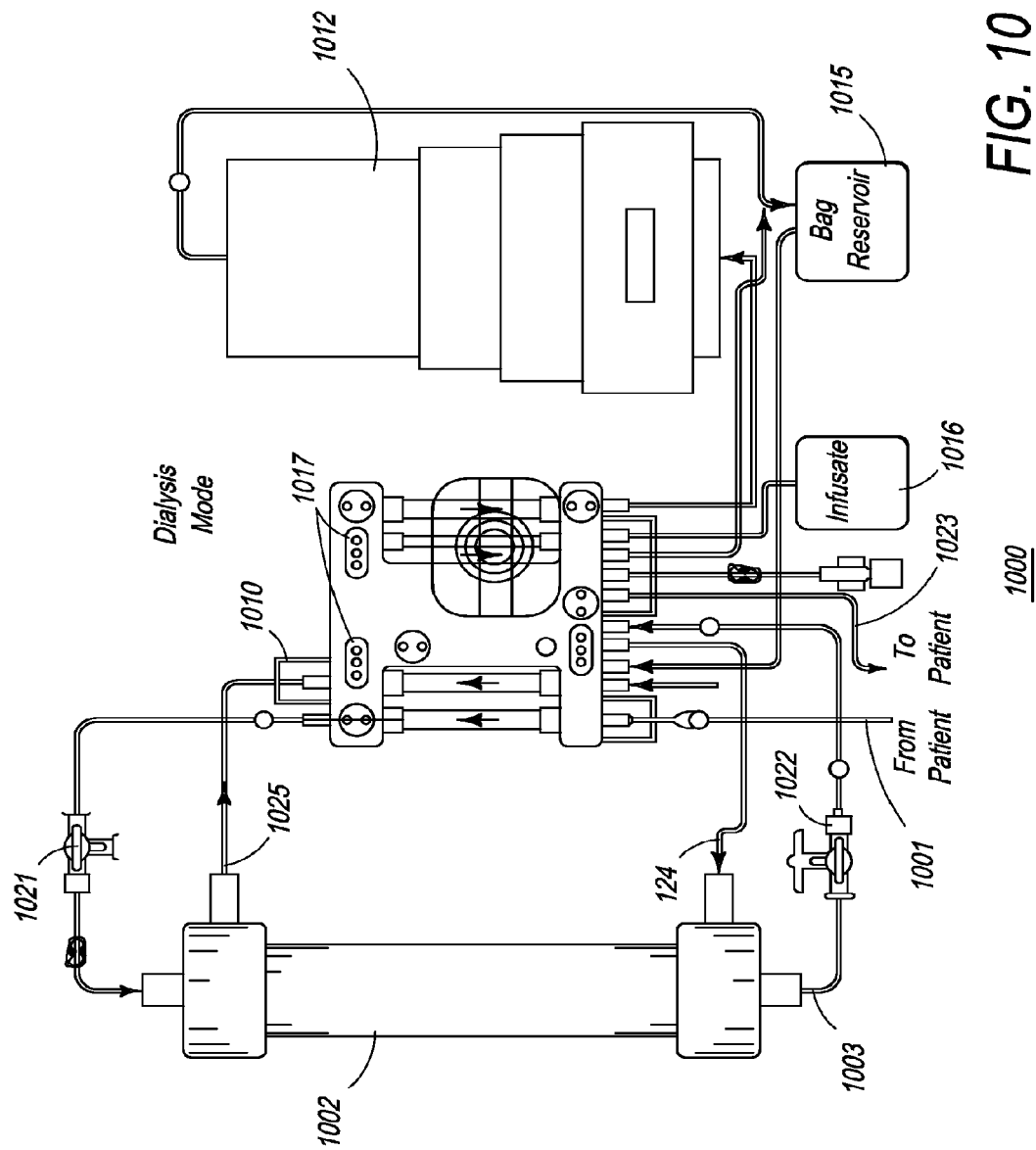
FIG. 10 is a schematic diagram showing one embodiment of the present invention in a dialysis mode.

The present invention can operate in at least two different modes: a priming mode and a treatment mode, which can comprise other modes of operation (such as hemodialysis, hemofiltration, or, simply, a non-priming mode). With respect to an exemplary treatment mode and referring concurrently to FIG. 4 and FIG. 10, a dialysis system 1000 operating in dialysis mode comprises a dialyzer 1002, 430, sorbent regeneration system (e.g. cartridge) 1012, manifold 1010, 400, infusate or dialysate source 1016 entering into the manifold 1010, 400 through Port M 425, and reservoir 1015 from which fresh dialysate is input back into the manifold 1010, 400 via Port E 419. In operation, blood enters the blood line 1001, into the manifold 1010, 400 through Port C 417, through a two-way valve 1021 which is in a first position, and into the dialyzer 1002. The purified blood exits the dialyzer 1002, 430, through a two-way valve 1022 which is in a first position, and into the manifold 1010, 400 through Port G 421. The blood passes through the manifold, passing through a plurality of valves, as described above in relation to manifold 400, 1010, and out of Port H 422 and into a blood line 1023 entering the patient.

Concurrently, infusate or dialysate passing from a source 1016 passes into the manifold 1010, 400, through Port M 425, through the manifold, out through Port F 420, into dialysate in-line 1024 and into dialyzer 1002, 430. After passing through the dialyzer 1002, the dialysate passes through an out-line 1025 and back into the manifold 1010, 400 through Port B 416 where it is routed to the sorbent-based dialysate regeneration system 1012 via Port N 426. Regenerated dialysate passes back through the manifold 1010, 430 via Port E 419 and recirculated through the dialyzer 1002, 430 with new dialysate, if and when required. To manage dialysate fluid flow, a reservoir 1015 is used to store regenerated dialysate, if and when needed. In one embodiment, the reservoir holds 5 liters of dialysate and has the capacity to hold up to 10 liters of dialysate and effluent from the patient.

Figure 11:
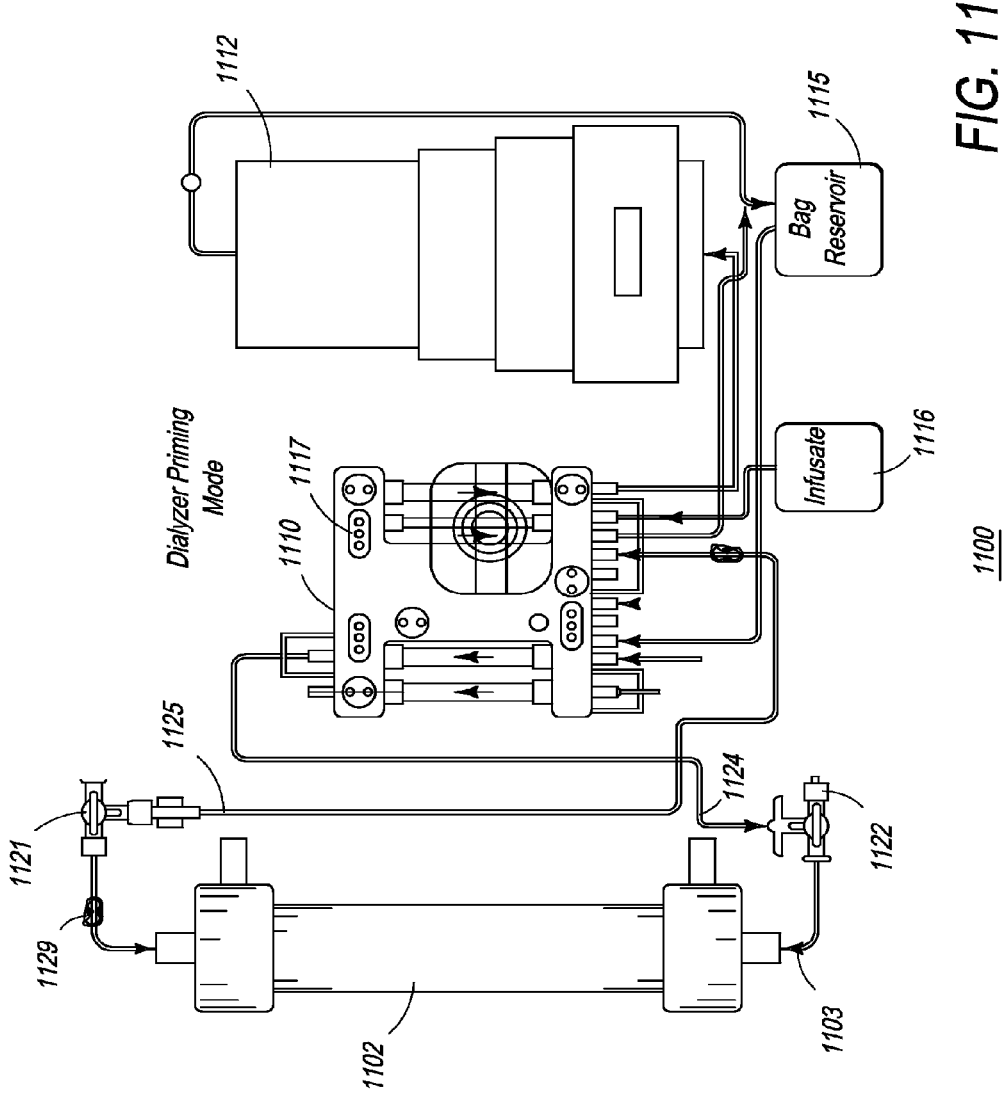
FIG. 11 is a schematic diagram showing one embodiment of the present invention in a dialysis priming mode.

With respect to an exemplary priming mode and referring concurrently to FIG. 4 and FIG. 11, a dialysis system 1100 operating in priming mode comprises a dialyzer 1102, 430, sorbent regeneration system (e.g. cartridge) 1112, manifold 1110, 400, infusate source 1116, and reservoir 1115. In operation, the bloodline from the patient (e.g. 1001 in FIG. 10) into the manifold 1110, 430 is not connected and therefore, no blood is flowing, or capable of flowing, through Port C 417 into the manifold 1110, 400. Rather, dialysate passing from a source 1116 passes into the manifold 1110, 430 through Port M 425, out through Port B 416 and through a dialysate in-line 1124, which is connected to the two-way valve port 1122.

In a preferred embodiment, a single two-way valve is incorporated into the physical body of the manifold and manipulated to switch between a treatment mode of operation and a priming mode of operation. In this embodiment, a manifold comprises a two-valve which, if activated or switched from a first positioned (e.g. closed) to a second position (e.g. open), causes a change to the internal flowpath of liquid within the manifold. As a result of this flowpath change, the blood and dialysate circuits, which, when the valve is closed, are fluidically isolated from each other, are now placed in fluid communication with each other. Preferably, no additional valves or switches need to be manipulated in order to achieve this state change, namely, to cause separate blood and dialysate circuits to become fluidly connected.

The valve switch may be effectuated by any means known in the art, including by physically manipulating a mechanical control on the surface of the manifold or electronically through the operation of a dialysis machine causing a change to the valve state through an interface between the dialysis machine, which has a controller to control the state of the valve in accordance with a user selected operational mode, and a valve interface integrated into the surface of the manifold. In one embodiment, the present invention deploys a bi-stable magnet-driven valve, as disclosed in U.S. patent application Ser. No. 12/351,969, filed on Jan. 12, 2009 and incorporated herein by reference.

In a preferred embodiment, the dialysis machine comprises an interface, in the form of a graphical user interface with touch screen buttons, physical keypad, or mouse, which can be manipulated to cause a dialysis machine, as shown in FIGS. 8 and 9, loaded with a manifold to start operation in either a treatment mode or priming mode. When instructed to operate in treatment mode, the controller generates a signal (in response to that treatment mode command) to cause the manifold valve to switch from an open, priming state to a closed, treatment state. When instructed to operate in priming mode, the controller generates a signal (in response to that priming mode command) to cause the manifold valve to switch from a closed, treatment state to an open, priming state. One of ordinary skill in the art would appreciate that all of the aforementioned control and user command functions are effectuated by incorporating one or more processors, executing programming embodying the aforementioned instructions, which are stored in local memory.

Referring to FIG. 4, in one embodiment, the two-way or two-state valve is preferably located at position "V" between the outlet of pump 403 and the outlet of pump 401. In treatment mode, the valve, which is in a closed position, permits dialysate fluid flowing out of pump 403 to circulate through the manifold, pass through Port F, and enter into the dialyzer 430. This dialysate circuit path is fluidically isolated from the blood circuit in which blood flows through pump 401 to circulate out of the manifold, pass through Port A, and enter into the dialyzer 430. Accordingly, in treatment mode, the valve ensures that the blood and dialysate circuits remain fluidly isolated.

In priming mode, the valve would be opened, thereby causing dialysate fluid flowing through pump 403 to pass through the manifold at Port A, into the dialyzer 430, out of dialyzer 430, and back into the manifold at Port G and out of manifold at Port H. Accordingly, in the priming mode, the valve ensures that the dialysate circulates through the blood circuit, thereby placing the blood and dialysate circuits in fluid communication. Functionally, the manifold is placed in priming mode, by manipulating the state of the two-way valve, preferably located at position "V" in the manifold.

After a specified volume of dialysate is pumped into and through the blood circuit, the two-way valve is closed. Pumping of dialysate may or may not continue. If continued, the fresh dialysate circulates through the dialysate circuit only. In the blood circuit, residual dialysate remains. To purge the dialysate from the blood circuit, a patient is connected to the "From Patient Line" 1001, shown in FIG. 10 and typically referred to as the arterial access line. The "To Patient Line" 1923, typically referred to as the venous return line is either held over a waste container or connected to a patient.

Placing the system in treatment mode, blood from the patient is drawn into the blood circuit, passing into the manifold via Port C, through pump 401, out of the manifold at Port A, through dialyzer 430, back to the manifold at Port G, and back out of the manifold at Port H. The blood thereby causes the residual priming fluid to be 'chased' through the blood circuit, removing any remaining air pockets in the process, and into either a waste container or the patient, depending on the connected state of the venous return line. After blood has completely filled the blood circuit, the system stops the blood pump or the user stops the pump manually. If not already connected, the venous return line is then connected to the patient and the treatment continues.

In another embodiment, a filter, such as a 0.22μ filter, can be used to help remove any remaining undesirable substances if the sorbent-canister is inadequate to produce essentially sterile dialysate. In one embodiment, the filter is positioned in-line with the reservoir input line, proximate to Port E of the manifold, and is used both during priming and operation.

By using this priming system, one avoids having to use an additional and separate set of disposables to just prime the blood side of the circuit. In particular, the present invention eliminates the need for a separate saline source, in particular a 1 liter bag of saline, and, accordingly, also eliminates the need for connectors and tubing to the separate saline source, including dual-lumen spikes or single lumen spikes used to connect blood lines to the saline.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

We claim:

1. A dialysis system comprising:
a housing comprising a panel;
a dialyzer;
a dialysate source;
a return line to a patient;
a rigid plastic manifold configured to be positioned on the panel, wherein the manifold defines a first flow path and a second flow path, wherein the first flow path defines a portion of a fluid pathway between the dialysate source and the dialyzer, and wherein the second flow path defines a portion of a fluid pathway between the dialysate source and the return line to a patient;
a first valve positioned in the manifold at an intersection of the first flow path and the second flow path, wherein, in a first state of the first valve, the first flow path is active and directs dialysate from the dialysate source to the dialyzer and wherein, in a second state of the first valve, the second flow path is active and directs dialysate from the dialysate source to the return line; and
an elastomeric material positioned in the manifold and over the first valve, wherein the elastomeric material is configured to cause the first valve to switch between the first state and the second state based upon an amount of pressure applied to the elastomeric material.

2. The dialysis system of claim 1 further comprising a second valve positioned in the second flow path between the first valve and a distal end of the return line.

3. The dialysis system of claim 2 wherein the second valve is closed when the first valve is in the first state and wherein the second valve is open when the first valve is in the second state.

4. The dialysis system of claim 1 wherein, when the dialysis system is in a hemodialysis mode of operation, the first valve is in the first state.

5. The dialysis system of claim 1 wherein, when the dialysis system is in a hemofiltration mode of operation, the first valve is in the second state.

6. The dialysis system of claim 1 further comprising a valve interface physically attached to the housing, wherein the valve interface is configured to apply the pressure to, or remove the pressure from, the elastomeric material to cause the first valve to switch between the first state and the second state.

7. The dialysis system of claim 1 wherein the second valve is a single state valve configured to either allow or stop fluid flow in the second flow path.

8. A dialysis system comprising:
a housing comprising a panel;
a dialyzer;
a first dialysate source;
a second dialysate source;
a return line to a patient;
a rigid plastic manifold configured to be positioned on the panel, wherein the manifold defines a first flow path and a second flow path, wherein the first flow path defines a portion of a fluid pathway between the first dialysate source and the dialyzer, and wherein the second flow path defines a portion of a fluid pathway between the second dialysate source and the return line to a patient;
a first valve positioned in the manifold at an intersection of the first flow path and the second flow path, wherein, in a first state of the first valve, the first flow path is active and directs dialysate to the dialyzer from the first dialysate source and wherein, in a second state of the first valve, the second flow path is active and directs dialysate from the second dialysate source to the return line; and
an elastomeric material positioned in the manifold and over the first valve, wherein the elastomeric material is configured to cause the first valve to switch between the first state and the second state based upon an amount of pressure applied to the elastomeric material.

9. The dialysis system of claim 8 further comprising a second valve positioned in the second flow path between the first valve and a distal end of the return line.

10. The dialysis system of claim 9 wherein the second valve is closed when the first valve is in the first state and wherein the second valve is open when the first valve is in the second state.

11. The dialysis system of claim 8 wherein, when the dialysis system is in a hemodialysis mode of operation, the first valve is in the first state and wherein, when the dialysis system is in a hemofiltration mode of operation, the first valve is in the second state.

12. The dialysis system of claim 8 further comprising a valve interface physically attached to the housing, wherein the valve interface is configured to apply the pressure to, or remove the pressure from, the elastomeric material to cause the first valve to switch between the first state and the second state.

13. The dialysis system of claim 8 wherein the second valve is a single state valve configured to either allow or stop fluid flow in the second flow path.

14. The dialysis system of claim 8 wherein the first dialysate source comprises a reservoir containing dialysate that is not sterile.

15. The dialysis system of claim 8 wherein the second dialysate source comprises a reservoir containing infusion grade dialysate.

16. A method for operating a dialysis system in a first mode or a second mode, wherein the dialysis system comprises a housing with a panel, a dialyzer, a first dialysate source, a second dialysate source, a return line to a patient, a rigid plastic manifold configured to be positioned on the panel, wherein the manifold defines a first flow path and a second flow path, wherein the first flow path defines a portion of a fluid pathway between the first dialysate source and the dialyzer, and wherein the second flow path defines a portion of a fluid pathway between the second dialysate source and the return line to a patient, and a first valve positioned in the manifold at an intersection of the first flow path and the second flow path, wherein, in a first state of the first valve, the first flow path is active and directs dialysate to the dialyzer from the first dialysate source and wherein, in a second state of the first valve, the second flow path is active and directs dialysate from the second dialysate source to the return line, the method comprising:

placing the dialysis system in the first mode;

in response to placing the dialysis system in the first mode, modifying an amount of pressure being applied to a diaphragm positioned in the manifold and over the first valve, wherein the diaphragm is configured to cause the first valve to switch between the first state and the second state based upon an amount of pressure applied to the diaphragm;

in response to placing the dialysis system in the first mode, directing dialysate from the first dialysate source to the dialyzer;

placing the dialysis system in the second mode;

in response to placing the dialysis system in the second mode, modifying the amount of pressure being applied to the diaphragm; and in response to placing the dialysis system in the second mode, directing dialysate from the second dialysate source to the return line.

17. The method of claim 16 further comprising activating a valve interface to modify the amount of pressure being applied to the diaphragm, wherein the valve interface is physically attached to the housing and configured to apply the pressure to, or remove the pressure from, the diaphragm to cause the first valve to switch between the first state and the second state.

18. The method of claim 16 wherein the first dialysate source comprises a reservoir containing dialysate that is not sterile and wherein the second dialysate source comprises a reservoir containing infusion grade dialysate.

19. The method of claim 16 further comprising a second valve positioned in the second flow path between the first valve and a distal end of the return line.

20. The method of claim 16 wherein the second valve is closed when the first valve is in the first state and wherein the second valve is open when the first valve is in the second state.

* * * * *